(12) United States Patent
Bannister et al.

(10) Patent No.: US 6,773,674 B2
(45) Date of Patent: Aug. 10, 2004

(54) THERMAL ANALYSIS FOR DETECTION AND IDENTIFICATION OF EXPLOSIVES AND OTHER CONTROLLED SUBSTANCES

(75) Inventors: William W. Bannister, Chelmsford, MA (US); Chien-Chung Chen, Dracut, MA (US); William A. Curby, Boston, MA (US); Eric B. Chen, Billerica, MA (US); Paul L. Damour, Bedford, NH (US); Antonio Morales, Bangor, ME (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 10/066,253

(22) Filed: Jan. 31, 2002

(65) Prior Publication Data

US 2004/0014233 A1 Jan. 22, 2004

Related U.S. Application Data

(62) Division of application No. 09/491,026, filed on Jan. 25, 2000, now Pat. No. 6,406,918.
(60) Provisional application No. 60/117,047, filed on Jan. 25, 1999.
(51) Int. Cl.[7] .......................... G01N 7/00; G01N 31/12; G01N 21/72; G01N 23/22; B32B 27/04
(52) U.S. Cl. ............................. 422/83; 422/78; 422/80; 422/147; 422/94; 73/23.36; 73/35.15; 73/35.16; 73/35.17; 436/155
(58) Field of Search ............................. 422/147, 78, 80, 422/82.12, 83, 94; 73/23.36, 35.15, 35.16, 35.17; 374/10, 11; 436/155

(56) References Cited

U.S. PATENT DOCUMENTS 3,643,491 A * 2/1972 Dell et al. ..................... 374/11
3,827,217 A * 8/1974 Volsy ............................. 96/51
4,202,200 A   5/1980 Ellson
4,248,084 A   2/1981 Bell et al.
4,317,360 A * 3/1982 Vasilenko et al. ............ 374/12
4,511,263 A   4/1985 Prosen
4,821,303 A * 4/1989 Fawcett et al. ................ 378/80
4,980,901 A  12/1990 Miller
4,987,767 A   1/1991 Corrigan et al.
5,006,299 A   4/1991 Gozani et al.
5,078,952 A   1/1992 Gozani et al.
5,092,218 A   3/1992 Fine et al.
5,109,691 A * 5/1992 Corrigan et al. ........... 73/23.36
5,138,889 A   8/1992 Conrad (List continued on next page.)

OTHER PUBLICATIONS

D.E.G. Jones, R.A. Augsten and K.K. Feng, Detection Agents for Explosives Journal of Thermal Analysis, vol. 44 (1995) 533–546.*

(List continued on next page.)

*Primary Examiner*—Jill Warden
*Assistant Examiner*—Brian Sines
(74) *Attorney, Agent, or Firm*—Fish & Richardson P.C.

(57) ABSTRACT

The invention features methods and systems for detecting the presence of an energetic material in a sample in which the presence of the energetic material is unknown. The method includes the steps of: heating the sample; measuring heat flow between the sample and its surrounding environment, e.g., by using differential scanning calorimetry (DSC); and analyzing the measured heat flow between the sample and its surrounding environment. An exothermal peak in the measured heat flow indicates the presence of the energetic material in the sample. The system includes a thermal measuring apparatus for performing the heating and measuring steps, and an analyzer for detecting the presence of the energetic material based on the measured heat flow. The invention also features methods and systems for identifying contraband materials (e.g., explosives and drugs) by measuring the thermogram (e.g., by DSC) of a sample to be identified and comparing it to reference thermograms for known contraband materials.

9 Claims, 17 Drawing Sheets

U.S. PATENT DOCUMENTS

| | | | |
|---|---|---|---|
| 5,224,775 A | * 7/1993 | Reading et al. | 374/11 |
| 5,300,888 A | * 4/1994 | Webster et al. | 324/315 |
| 5,313,061 A | * 5/1994 | Drew et al. | 250/281 |
| 5,345,809 A | 9/1994 | Corrigan et al. | |
| 5,346,306 A | * 9/1994 | Reading et al. | 374/10 |
| 5,356,217 A | * 10/1994 | Sheffield | 374/45 |
| 5,638,166 A | 6/1997 | Funsten et al. | |
| 5,668,342 A | 9/1997 | Discher | |
| 5,760,898 A | 6/1998 | Haley et al. | |
| 5,826,983 A | * 10/1998 | Nakamura et al. | 374/14 |
| 5,981,290 A | * 11/1999 | Lyon et al. | 436/157 |
| 6,210,035 B1 | * 4/2001 | Nakamura | 374/11 |
| 6,331,074 B1 | * 12/2001 | Kimura | 374/10 |

OTHER PUBLICATIONS

Jones et al., "Detection Agents for Explosives," Journal of Thermal Analysis, 44:533–546, 1995.

Jones et al., "Characterization of DMNB, A Detection Agent for Explosives, By Thermal Analysis and Solid State NMR," *Journal of Thermal Analysis,* 44:547–561, 1995.

Kolla, "The Application of Analytical Methods to the Detection of Hidden Explosives and Explosive Devices," *Angew. Chem. Int. Ed. Engl.,* 36:800–811, 1997.

R.C. Mackenzie, ed., *Differential Thermal Analysis,* vol. 2, pp. 353–377, Academic Press, London, 1972.

Reading et al., "Thermal Analysis for the $21^{st}$ Century," *American Laboratory,* TA244:13–17, Jan. 1998.

Stoller, "More Detectors Prowl Baggage, but not Enough," *USA Today,* pp. 1B–2B, Feb. 18, 1998.

J. Yinon et al., *The Analysis of Explosives,* pp. 133–141, Pergamon Press, Oxford, 1981.

P.D. Garn, *Thermoanalytical Methods of Investigation,* pp. 291–293, Academic Press, New York 1965.

W.W. Wendlandt, *Thermal Methods of Analysis,* 2nd Ed., pp. 129–131, John Wiley and Sons, New York, 1974.

W.W. Wendlandt, *Thermal Methods of Analysis,* 2nd Ed., pp. 265–269, John Wiley and Sons, New York, 1974.

* cited by examiner

DSC thermogram of charcoal, sample weight is 0.04 mg

DSC thermogram of C-4, sample weight is 0.308 mg

DSC thermogram of HMTD, sample weight is 0.44 mg

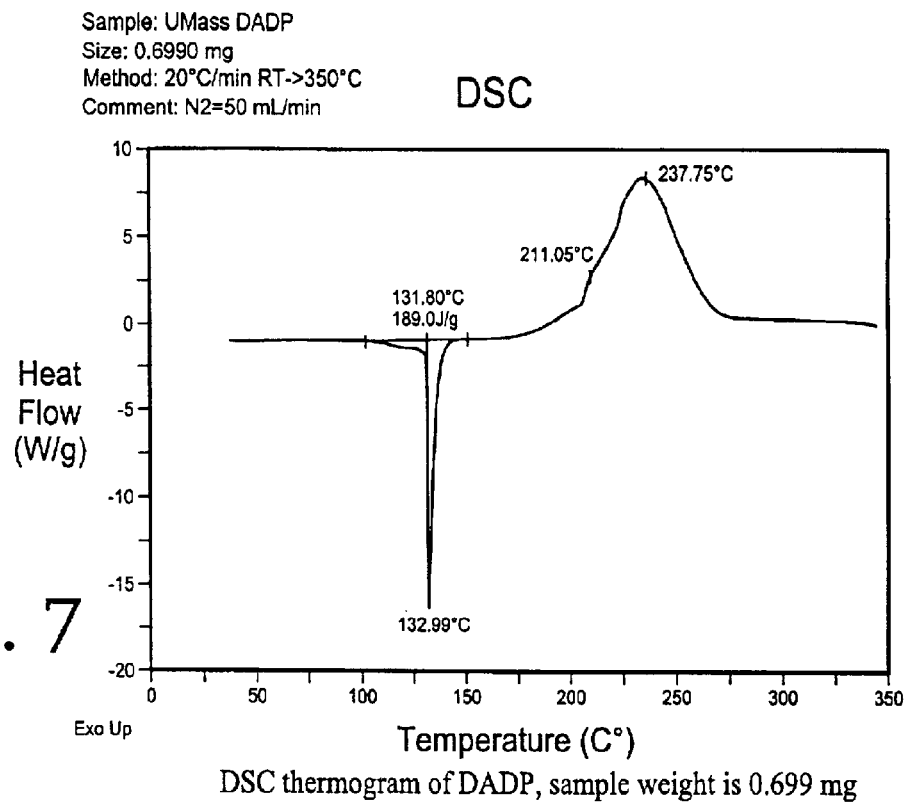
DSC thermogram of DADP, sample weight is 0.699 mg
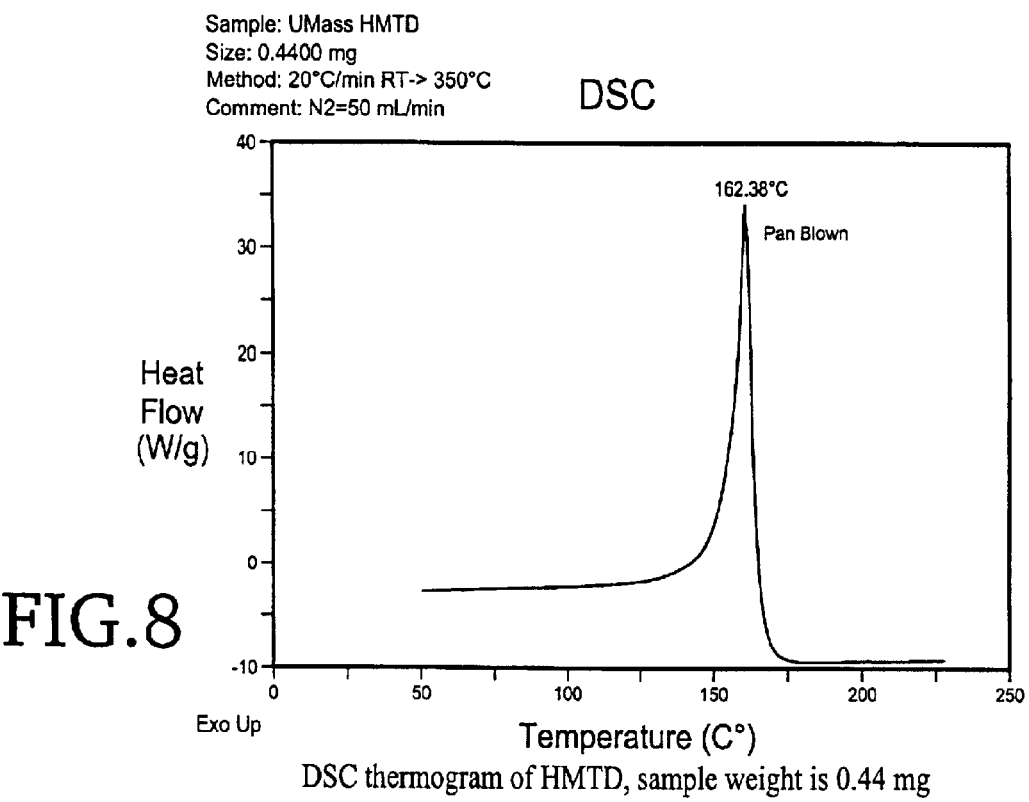
DSC thermogram of HMTD, sample weight is 0.44 mg DSC thermogram of Ammonium Nitrate, sample weight is 0.09 mg DSC thermogram of Urea Nitrate, sample weight is 0.211 mg DSC thermogram of Ammonium Perchlorate, sample weight is 0.444 mg DSC thermogram of Benzoyl Peroxide, sample weight is 0.071 mg DSC thermogram of RDX, sample weight is 0.400 mg DSC thermogram of Black Powder, sample weight is 0.489 mg DSC thermogram of Smokeless Remington,, sample weight is 0.071 mg DSC thermogram of Mil. Spec. Ammo., sample weight is 0.215 mg DSC thermogram of 2,3-dimethyl1-2,3-dinitrobutane, sample weight is 0.184 mg DSC thermogram of C4/Water/Charcoal, sample weight is 12.3 mg DSC thermogram of DADP/Water/Charcoal, sample weight is 11.1 mg DSC thermogram for Charcoal/Skin Fragments, and for Charcoal/Skin/C4 mixture MicroDSC of RDX with heating rate of 5°C/sec MicroDSC of TATP MicroDSC of HMTD MicroDSC of RDX with heating rate of 25°C/sec DSC thermogram of Sugar, sample weight is 0.071 mg DSC thermogram of caffeine, a non-explosive, sample weight is 0.904 mg DSC thermogram of Bupivacaine, sample weight is 0.321 mg DSC thermogram of Tetrcaine, sample weight is 0.581 mg

THERMAL ANALYSIS FOR DETECTION AND IDENTIFICATION OF EXPLOSIVES AND OTHER CONTROLLED SUBSTANCES

This application is a divisional of U.S. application Ser. No. 09/491,026, filed Jan. 25, 2000, now U.S. Pat. No. 6,406,918, which is a continuation of U.S. Provisional Application No. 60/117,047, filed Jan. 25, 1999.

FIELD OF THE INVENTION

The invention relates to the detection and identification of explosives and other controlled substances.

BACKGROUND OF THE INVENTION

To protect public safety and prevent terrorist activity it is important to detect hidden explosives. For example, many airports routinely use x-ray scanning systems to identify explosives or other violent weapons hidden within baggage. Also, airports and bomb squads routinely use "sniffing" detection devices that absorb particulate or vapor matter and analyze the matter for the presence of explosives. Analytical techniques used by such detection devices include ion mobility spectrometry (IMS) and gas chromatography.

Explosives can be made from a wide range of energetic materials including, e.g., organic nitrates, organonitro compounds, ketone and acyl peroxides, inorganic chlorates, perchlorates, nitrates, fulminates, and acetylides. Unfortunately, because of the wide range of energetic materials and the many differences in their physical properties, several detection devices detect only certain types of explosives and fail to detect others. For example, many detection devices readily detect conventional explosives made of organic nitro and nitrate compounds, but fail to detect explosives made of inorganic nitrates or non-nitrogeneous compounds. In particular, many nitrogen-based detection devices fail to detect explosives such as ANFO (ammonium nitrate in fuel oil), Black Powder ("gun powder" formed from potassium nitrate, sulfur, and charcoal), and triacetone triperoxide (TATP). As a result, such explosives are sometimes referred to as "transparent." Moreover, TATP, for example, can be easily prepared in a basement lab using commercially available starting materials obtained from, e.g., hardware stores, pharmacies, and stores selling cosmetics, and can be as or more powerful than military analogs.

In addition to detecting hidden explosives, it is also desirable to identify the particular type of explosive once it is detected to assess its danger, deactivate it, and/or provide forensic evidence.

Detection and identification of other controlled substances such as narcotic drugs is also important. To insure public safety, law enforcement officials try to detect and identify hidden quantities of narcotic drugs. Where possible, law enforcement officials also try to provide proper identification of the detected drugs as forensic evidence.

SUMMARY OF THE INVENTION

The invention features methods and systems for detecting the presence of an explosive in a sample of unknown material. The methods and systems are based in part on the recognition that all self-contained explosives decompose and release significant amounts of energy upon thermal excitation, whereas most other materials absorb energy upon thermal decomposition. The released energy can be used to detect small quantities of explosive hidden in a sample of unknown composition. Thus, the presence of an explosive in a unknown sample can be detected by thermally analyzing the unknown sample to produce a thermogram and determining whether the thermogram includes a strong exotherm to indicate the presence of the explosive. In particular embodiments it is preferable that the thermal analysis take place in a substantially anaerobic environment to minimize exothermic reactions with oxygen. Various methods can be used to conduct the thermal analysis including differential thermal analysis (DTA), quantitative differential thermal analysis (QDTA), dynamic differential calorimetry (DDC), dynamic enthalpic analysis (DEA), thermogravimetric analysis (TGA), and differential scanning calorimetry (DSC).

In another aspect, and in addition to detecting the general presence of an explosive in an unknown sample, the new methods and systems can identify the specific type of explosive by comparing the measured thermogram for the unknown sample to reference thermograms for particular types of explosives. Similarly, the presence of a particular drug or any other contraband material in a sample of unknown composition can be detected and identified by comparing the sample thermogram to reference thermograms for particular types of drugs and contraband materials, e.g., cocaine and heroin.

In general, in one aspect, the invention features a method for detecting the presence of an energetic material in a sample in which the presence of the energetic material is unknown. The method includes the steps of: heating the sample; measuring heat flow between the sample and its surrounding environment, e.g., by using differential scanning calorimetry; and analyzing the measured heat flow between the sample and its surrounding environment. An exothermal peak in the measured heat flow indicates the presence of the energetic material in the sample.

The heating step can include heating the sample from about room temperature to a temperature of at least 200° C., but, in some embodiments, not greater than about 550° C., and in other embodiments, not greater than about 350° C. Alternatively, or in addition, the heating step can include heating the sample in a substantially anaerobic environment.

In some embodiments, the sample includes a plurality of particles, which can be collected from air samples, surfaces of passenger clothing, luggage, and cargo. In particular, to prevent terrorist activities, the sample can be collected from an airport environment.

In another aspect, the invention features a system for detecting the presence of an energetic material in a sample in which the presence of the energetic material is unknown. The system includes: a thermal measuring apparatus (e.g., a differential scanning calorimeter) which during operation heats the sample and measures heat flow between the sample and its surrounding environment; and an analyzer coupled (e.g., electrically) to the thermal measuring apparatus which during operation analyzes the heat flow measured by the thermal measuring apparatus to determine the presence or absence of an exothermal peak. The presence of an exothermal peak indicates the presence of the energetic material in the sample and the absence of an exothermal peak indicates the absence of any energetic material in the sample.

The thermal measuring apparatus can be configured to heat the sample from about room temperature to a temperature of at least 200° C., but, in some embodiments, not greater than about 550° C., and in other embodiments, not greater than about 350° C. Alternatively; or in addition, the thermal measuring apparatus can be configured to heat the sample in a substantially anaerobic environment.

The detection system can also include a collection apparatus that collects and concentrates the sample, e.g., by electrostatic precipitation or by solvent extraction with a volatile organic solvent.

In general, in another aspect, the invention features a method for identifying the presence of a contraband material (e.g., an explosive or illegal drug) in a test sample in which the presence of the contraband material is unknown. The identification method includes: heating the test sample; measuring heat flow between the test sample and its surrounding environment to produce a test thermogram, e.g., by using differential scanning calorimetry; and comparing features of the test thermogram to features of reference thermograms for reference samples including known contraband materials. A match of a reference thermogram with the test thermogram identifies the presence of a contraband material. To determine such a match, the temperatures of exotherms, endotherms, or both exotherms and endotherms, in the thermogram of the test sample can be compared with the temperatures of exotherms, and endotherms in the reference thermograms. In some embodiments, the sample is heated in a substantially anaerobic environment.

In yet another aspect, the invention features a system for identifying the presence of a contraband material (e.g., an explosive or an illegal drug) in a test sample in which the presence of the contraband material is unknown. The identification system includes: a thermal measuring apparatus (e.g., a differential scanning calorimeter) which during operation heats the test sample, measures heat flow between the test sample and its surrounding environment, and records a test thermogram of the test sample based on the measured heat flow; and an analyzer coupled to the thermal measuring apparatus which during operation compares features of the test thermogram to features of one or more reference thermograms for reference samples including known contraband materials and determines whether there is a match between a reference thermogram and the test thermogram to identify the presence of a contraband material. The system can further include a collection system that collects and concentrates the sample.

The reference thermogram stored in the analyzer can be that of an explosive or a drug. In addition, the analyzer can store a set of reference thermograms. Also, to determine the match, the analyzer can compare the temperatures of exotherms, endotherms, or exotherms and endotherms in the thermogram of the test sample with temperatures of exotherms and endotherms in the reference thermograms.

Energetic materials are materials that undergo exothermal decomposition in an anaerobic environment. Explosives are a subset of energetic materials in which the exothermal decomposition is rapid and self-sustaining, releasing large amounts of heat and pressure. The exothermal decomposition for energetic materials and explosives can be triggered by heat and/or mechanical shock. An anaerobic environment is an environment in which oxygen is absent. A substantially anaerobic environment can be produced by purging an enclosed chamber with an inert gas, e.g., nitrogen, or continuously flowing the inert gas through an open chamber. Under such conditions, the environment can contain less than about 1 percent of oxygen.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The new methods and systems described herein provide a number of advantages. For example, they can detect the presence of a very broad range of explosives, including explosives such as ANFO, Black Powder, and TATP, which are "transparent" to conventional explosive detection methods. In particular, since the detection is based on the presence of an exotherm in a thermogram, which is a general feature of any energetic material, the methods and systems can, in principle, detect the presence of any explosive in an unknown sample. Furthermore, the methods and systems can employ relatively inexpensive, commercially available instruments, such as differential scanning calorimeters (DSCs). Depending on the desired application, such instruments can be selected for rapid thermal analysis and explosive identification such as would be necessary at passenger and baggage gates at airports. Alternatively, cheaper but less rapid instruments can be used in forensic detection of explosives, drugs, or contraband materials.

Other features and advantages of the invention will be apparent from the following detailed description, and from the claims.

BRIEF DESCRIPTION OF THE DRAWING

FIGS. 3 to 24 are differential scanning calorimetery thermograms relating to the detection and identification of various explosives.

DETAILED DESCRIPTION

The invention features methods and systems for determining the presence of explosives, drugs, or contraband agents in an unknown sample using thermal analysis.

Thermal Analysis

Generally, thermal analysis monitors heat flow to, or from, a sample. In one example, thermal analysis involves measuring the temperature of a sample as a function of time as the sample is allowed to warm (or cool) to the temperature of its environment. The rate at which the sample warms (or cools) can change abruptly at particular temperatures when the sample undergoes a phase transition (e.g., melting or thermal decomposition of one or more components of the sample). Such phase transition temperatures are characteristics of the sample and a curve illustrating at least a portion of the time-dependent temperature of the sample can be used as a signature of the sample for a particular measurement protocol. In another example, thermal analysis involves measuring the heat flow required to heat (or cool) a sample at a steady or prescribed rate as a function of temperature. Once again, when the sample undergoes phase transitions, the amount of heat flow required to heat (or cool) a sample can change abruptly. The temperatures at which such abrupt changes occur (e.g., the phase transition temperatures) and the magnitudes of the changes are characteristic signatures of the sample. In many examples, the thermal measurements involve a differential analysis in which changes in heat flow to, or from, a measurement sample is compared to corresponding changes in a reference sample. For a general discussion of thermal analysis, see, e.g., R. C. Mackenzie, *Differential Thermal Analysis* (Academic Press, London, 1972).

In general, thermal analysis can be done by a number of various techniques including differential thermal analysis (DTA), quantitative differential thermal analysis (QDTA), dynamic differential calorimetry (DDC), dynamic enthalpic analysis (DEA), thermogravimetric analysis (TGA), and differential scanning calorimetry (DSC).

DSC is a technique in which the difference in energy input (e.g., heat flow) into a measurement sample and a reference sample is measured as a function of temperature while the measurement and reference samples are subjected to a controlled temperature program. The resulting energy versus temperature curve is an example of a thermogram. Alternatively, the thermogram can be an energy versus time curve, where the temperature is changing as a function of time in response to a prescribed heating or cooling program.

Figure 1:
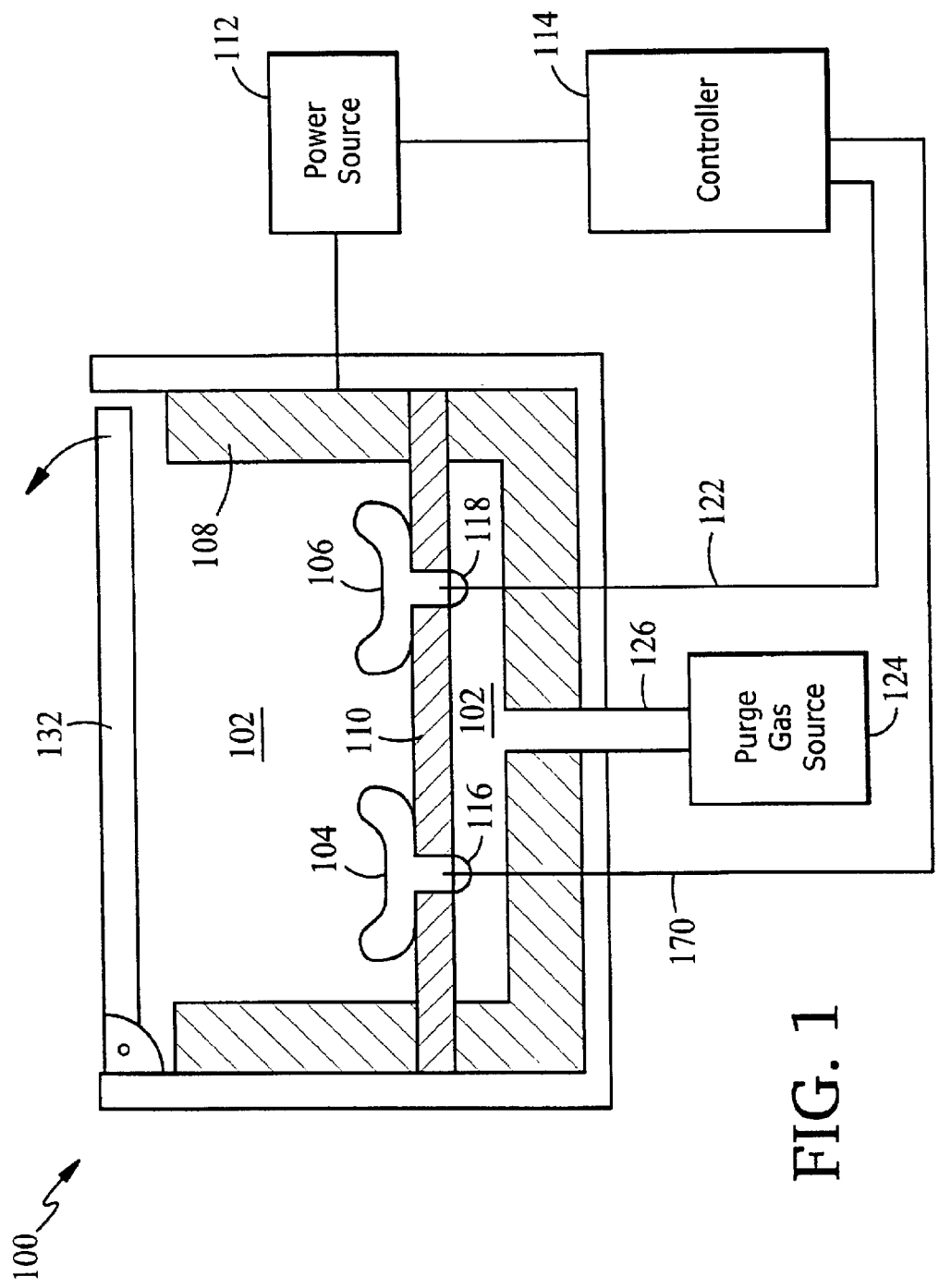
FIG. 1 is a schematic of a differential scanning calorimeter.

A schematic of one example of a differential scanning calorimeter 100 is shown in FIG. 1. The calorimeter includes a sample chamber 102 having a reference pan 104 and a measurement pan 106 for the reference and measurement samples, respectively. A heating block 108 surrounds sample chamber 102 and connects to a thermoelectric disk 110, which supports pans 104 and 106. A power source 112 provides electrical energy to disk 110 that causes disk 110 to equally heat pans 104 and 106. A controller 114 controls power source 112 such that the heat generated at pans 104 and 106 can be user-specified and can follow a prescribed program. Thermocouples 116 and 118 monitor the temperature of the reference and measurement pans 104 and 106, respectively, and sends signals 120 and 122 indicative of those temperatures to controller 114. A purge gas source 124 (e.g., nitrogen) connects to sample chamber 102 through inlet 126 to purge, during operation, oxygen from the sample chamber and thereby create an anaerobic environment within the sample chamber. A lid 132 permits introduction and removal of the reference and measurement samples from pans 104 and 106. In many applications, the reference pan is left empty so that the reference sample is simply the gas in the ambient environment, e.g., nitrogen or air.

During operation, the measurement sample is placed in the measurement pan and the sample chamber is purged with nitrogen. Then, controller 114 executes a prescribed heating program, e.g., constant heating, and records the overall temperature T of sample chamber 102 based on the average of the temperatures measured by thermocouples 116 and 118. Controller 114 also records the temperature differential $\Delta T$ between the measurement and reference samples based on the difference between the temperatures measured by thermocouples 116 and 118. Although the thermoelectric disk heats the samples evenly, thermally activated physical changes (e.g., a phase transition) in one but not the other of the two samples can release or absorb heat, thereby producing a non-zero temperature differential between the samples. It is these types of thermally activated changes that can be characterized by DSC.

For example, if the measurement sample includes a component not present in the reference sample, as the overall temperature of the sample chamber passes through the melting point of the component, the temperature of the measurement sample lags that of the reference sample as the component melts. Thus, the recorded thermogram (i.e., the plot of $\Delta T$ versus T recorded by the controller) will include a peak at the melting temperature of the component.

As is well known, melting and vaporization are phase transitions that absorb energy from the environment, i.e., they are endothermic. Other types of physical change, e.g., freezing, can release energy to the environment, i.e., they are exothermic. In general, explosives and energetic material decompose exothermically, whereas other materials decompose endothermally. Chemical reactions between non-energetic material can, however, be either exothermic or endothermic. For example, materials that burn in the presence of oxygen, i.e., combustion reactions, are exothermic. In addition, many oxidation reactions are exothermic. To limit thermal contributions to the thermogram caused by reactions between the sample and oxygen, the sample chamber can be purged with an inert gas such as nitrogen to produce a substantially anaerobic environment. Alternatively, the temperature range of the thermal analysis can be kept below minimum temperatures required for such exothermal reactions involving oxygen. For example, the maximum temperature can be kept below about 600° C., 500° C., 450° C., 400° C., or even below about 350° C., to limit thermal contributions to the thermogram caused by reactions between the sample and oxygen in the chamber. The maximum temperature for the thermal analysis scan should be high enough that the sample decomposes, but low enough that the sample does not combust.

Differential scanning calorimeters can differ from the schematic of FIG. 1. In other embodiments, the reference and measurement pans are heated by separate heaters that are operated by a servo-control system to minimize the temperature differential between the pans. A controller measures the difference in energy provided by the heaters to minimize the temperature differential as a function of the overall average temperature.

Detection of Explosives

A general property of all self-contained explosives is that they release considerable amounts of energy, even in the absence of oxygen, upon excitation by an external source of energy such as heat, friction, or impact. In contrast, non-explosives typically absorb energy when thermally decomposed in an anaerobic environment. The contrast is striking when one considers that when burnt in the presence of oxygen (at temperatures greater than about 600° C.), sugar, a non-explosive, releases more heat (heat of combustion equal to −3,900 kcal/kg) than that of trinitrotoluene (TNT) (heat of combustion equal to −3,600 kcal/kg). However, TNT is much more unstable than sugar and will spontaneously release large amounts of its internal energy upon excitation by a relatively low input of initiation energy, even in the absence of oxygen in external air. In other words, TNT and other explosives undergo strong exothermal decomposition in an anaerobic environment when thermally excited. In contrast, and like most other stable compounds, sugar will decompose endothermically when thermally excited in an anaerobic environment.

Even in sample chambers containing oxygen, stable compounds will typically exhibit only endothermic transitions provided that the temperature is kept below a minimum threshold value required for exothermal reactions with oxygen. For example, many exothermal reactions with oxygen require temperatures in excess of about 500° C., or at least in excess of about 350° C. or 400° C. Thus, the explosives detection can also be performed in the presence of oxygen, however, in many cases the temperature should be less than about 500° C., and in some cases, less than about 350° C. or 400° C.

Samples of interest can thus be divided into two general categories: 1) energetic materials such as explosives—high energy, low stability compounds that exothermically decompose with heat; and 2) stable materials that endothermically decompose with heat. Such stable compounds include volatile alcohols, ketones, acids, esters, aldehydes, amines, and other compounds that are commonly found in, e.g., cosmetics, beverages, and condiments.

When trying to detect explosives in public places such as airports, products such as cosmetics, beverages, and condiments are examples of the types of innocuous materials that must be differentiated from explosive agents that would be used in a terrorist attack. Without exception, all of these innocuous species will thermally decompose endothermically in the absence of air, although some may be more unstable than others and have lower decomposition temperatures.

Figure 2:
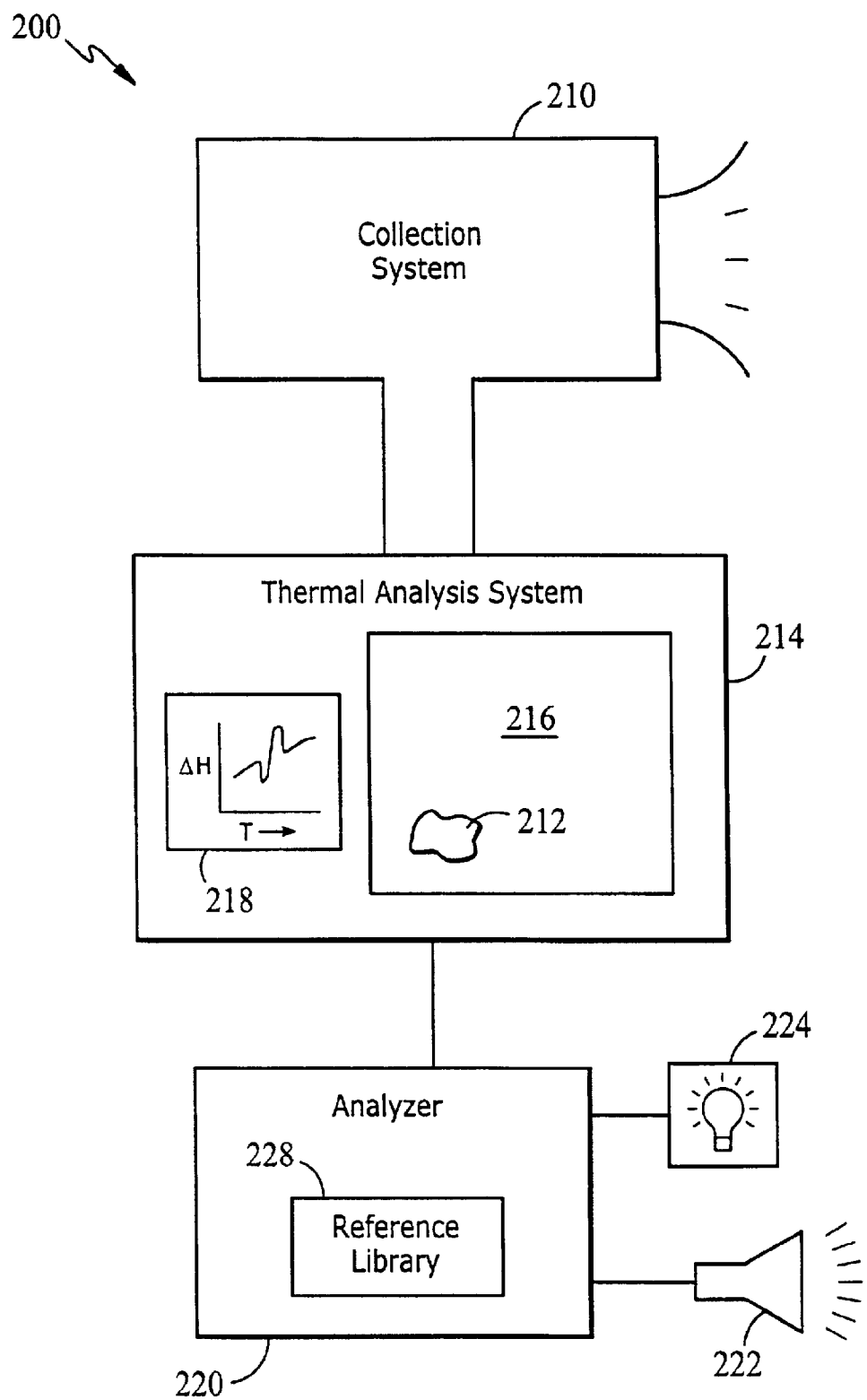
FIG. 2 is a schematic of an explosives detector.

FIG. 2 is a schematic of an explosives detector 200 that exploits this property. A collection system 210 gathers particles or vapors from objects that potentially contact or contain explosives. For example, the collection apparatus can be a hand-held vacuum that collects particles, e.g., from luggage or passenger's clothing, on a filter and condenses the particles on the filter into a sample 212, whose composition is unknown. Collection system 210 delivers sample 212 to an anaerobic chamber 216 in a thermal analysis apparatus 214, such as a differential scanning calorimeter. Thermal analysis apparatus 214 generates a thermogram 218 of sample 212 under anaerobic conditions sends a signal 219 indicative of the thermogram to an analyzer 220. Based on signal 219, analyzer 220 determines whether thermogram 218 includes a strong exothermal peak. If analyzer 220 finds such a peak, it signals that an explosive is present in the unknown sample 212 using, e.g., an alarm 222 or visual display 224. Thereafter, if necessary, the operator can conduct a more thorough search of the articles from which the sample was collected.

Alternatively, as described above, chamber 216 need not be anaerobic provided that the temperature in the chamber be kept less than temperatures at which exothermal oxidative or combustive reactions occur.

As described in greater detail below, suitable collection systems and thermal analyzers are commercially available. The analyzer can be a computer connected to the thermal analysis system and operating appropriate software, a dedicated electronic circuit embedded in the thermal analysis system, or some other similar electronic component. For example, in one embodiment the thermal analysis apparatus could measure the thermogram and send a signal carrying the thermogram information to a computer, which stores software, e.g., on a hard-disk or CR-ROM, for analyzing the thermogram. The thermogram typically consists of a series of data correlating heat transfer, e.g., as measured by a temperature difference between test and reference samples, to temperature. The software causes the processor in the computer to analyze the series of data and identify whether the data includes an exothermal peak. Such software is commercially available from TA Instruments, Inc. (New Castle, Del.). Alternatively, suitable software can be programmed by those skilled in the art using, e.g., standard programming languages such as C, C++, or Visual Basic, a general purpose interfaces bus (GPIB) with standard IEEE-488 software, and packaged software routines, such as those found in *Numerical Recipes in C: The art of Scientific Computing* by William H. Press et al. (Cambridge University Press, 1993). For example, the presence of an exothermal peak may be identified as, e.g., at least a 1% increase in heat flow followed by at least a 1% decrease in heat flow, or at least a 10% increase in heat flow followed by at least a 10% decrease in heat flow, over a span of, e.g., about 5 to 20° C. In practice, however, the presence of an exothermal peak may depend on the particular parameters (e.g., heating rate) of the thermal analysis apparatus and the particular explosives of interest. If the computer identifies an exothermal peak, it confirms the presence of an energetic material in the test sample, otherwise it confirms that no energetic material is present in the test sample.

Many of the explosives that may be anticipated in potential terrorist encounters release large amounts of thermal energy following non-oxidative thermal decomposition. Thus, relatively small quantities of an explosive in a sample collected by collection system 210 can produce a detectable exotherm. For example, C4 is a plastic explosive formed largely (about 90%) of Trimethylenetrinitramin, a military plastic explosive given the acronym RDX, and about 10% plastic binder and other species in small quantities. Anaerobic heating of less than 1 milligram of C4 will release sufficient heat as to be readily detected with inexpensive, conventional differential scanning calorimeters or other differential thermal analysis equipment. Furthermore, as described in greater detail below, recently developed micro-differential scanning calorimeters (microDSCs) such as Model 2990 from TA Instruments, Inc., (New Castle, Del.) can reduce the required quantity of detectable explosive to picogram amounts with rapid (about 4 seconds) detection times.

To demonstrate the detectability of explosives based on thermal analysis, DSC thermograms were measured for a number of energetic and non-energetic agents using a conventional differential scanning calorimeter (TA Instrument, Inc. DSC 2910). A small amount (from 0.05 to 0.7 mg) of each agent was sealed in an air-tight DSC sample container and placed in the DSC. Air was used as the reference sample. The agents were introduced into the sample containers in an ambient environment and as a result the containers included small amounts of oxygen together with the respective agents. A thermogram was measured for each sample by scanning the temperature of the sample from room temperature to about 400° C. at a rate of about 20° C./min. The sample chamber was continuously purged with nitrogen flowing at a rate of about 50 ml/min.

In other embodiments, the agents can be introduced into the sample containers in an anaerobic environment, thereby preventing the introduction of oxygen. Furthermore, in additional embodiments, the sample containers do not need to be sealed and can be exposed to the environment within the sample chamber of the DSC, which is preferably purged with nitrogen, but can also include oxygen.

DSC Patterns for Non-Energetic Species

Charcoal and isopropanol were selected as examples of non-energetic species. Isopropanol may be frequently encountered in an airport setting since it is a common component in cosmetics and other personal products. The thermograms for charcoal and isopropanol are shown in FIGS. 3 and 4, respectively.

Figure 3:
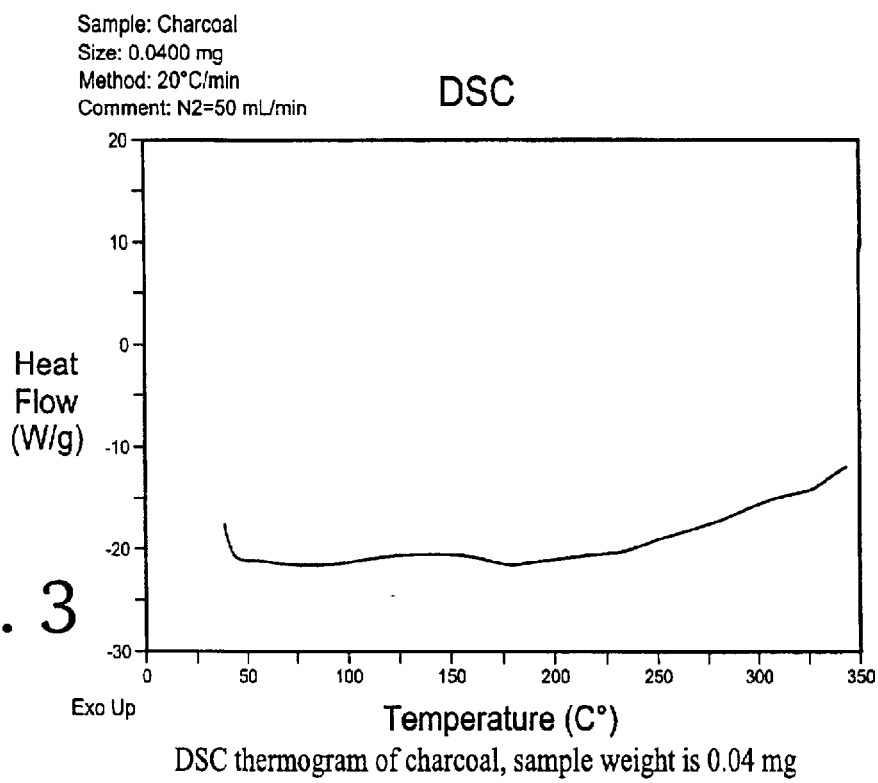
Figure 4:
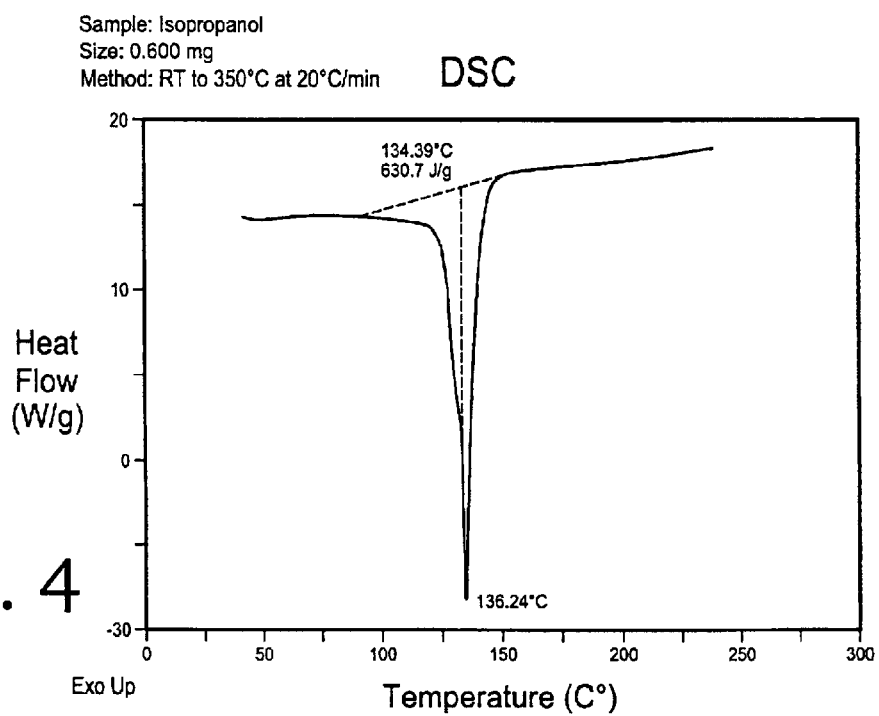

FIG. 3 shows that the thermogram for charcoal exhibits a gentle, upward sloping base line, with a few depressions indicating minor thermal desorptions of absorbed gases in the charcoal. FIG. 4 shows that the thermogram for isopropanol includes an endothermic peak at about 138° C., corresponding to the boiling point of isopropanol. The boiling point is shifted to a higher temperature than that in an ambient environment due to increased pressure in the sealed DSC sample container. No other thermal transitions were observed above those temperatures.

In general, the exothermal detection can be easily performed at temperatures up to about 300° C., 350° C., or 400° C. with most non-energetic species not decomposing, and if so, doing so endothermically. More often, endothermic peaks result from endothermic physical changes such as melting, boiling, degassing, or sublimation.

DSC Patterns for Energetic Species

Figure 5:
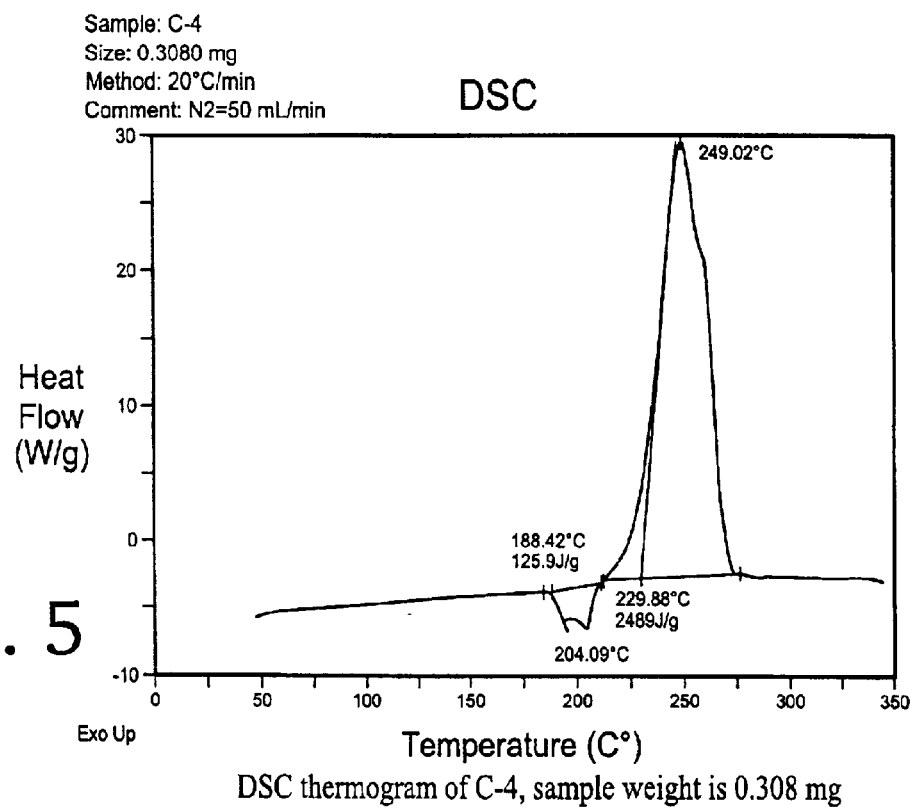
Figure 6:
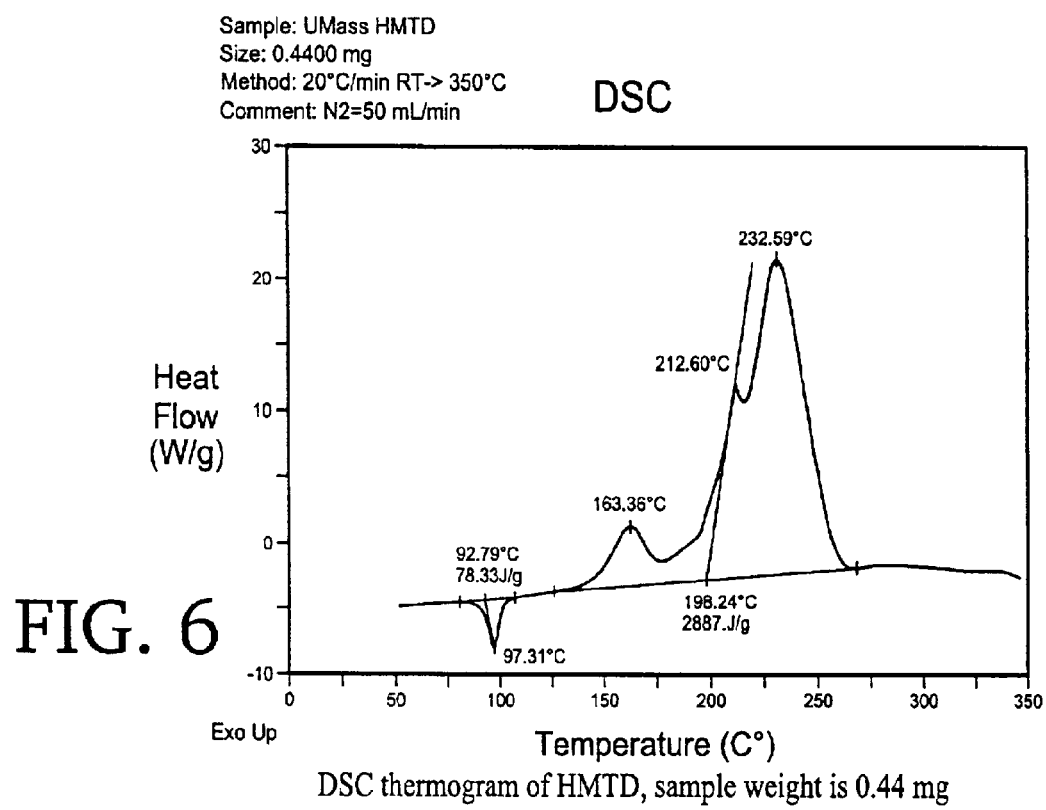
Figure 9:
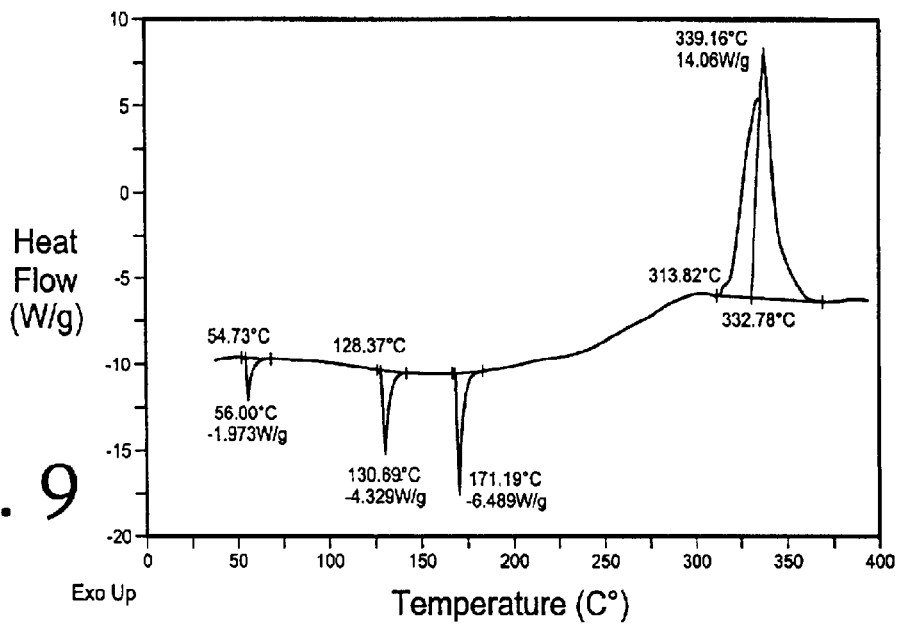
Figure 10:
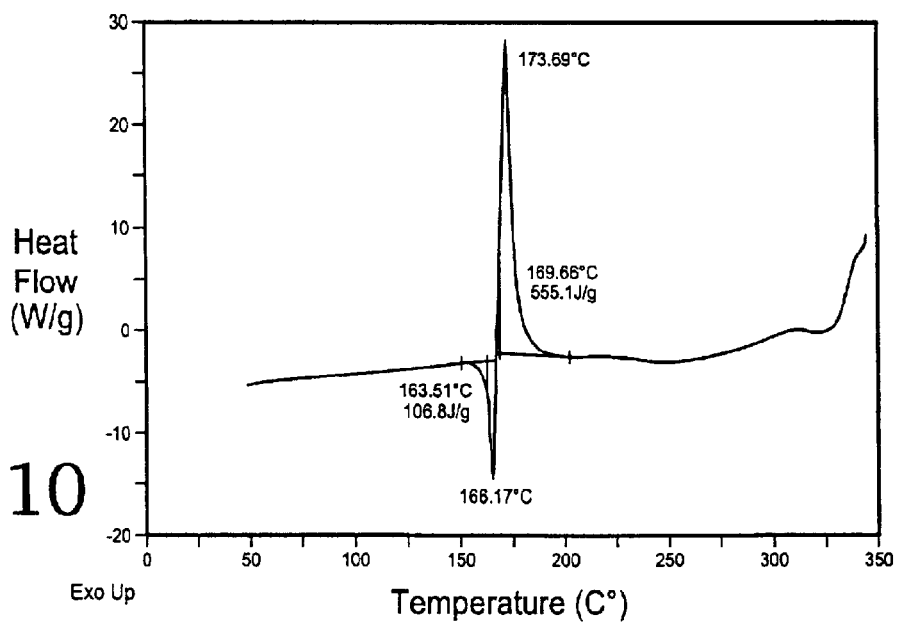
Figure 11:
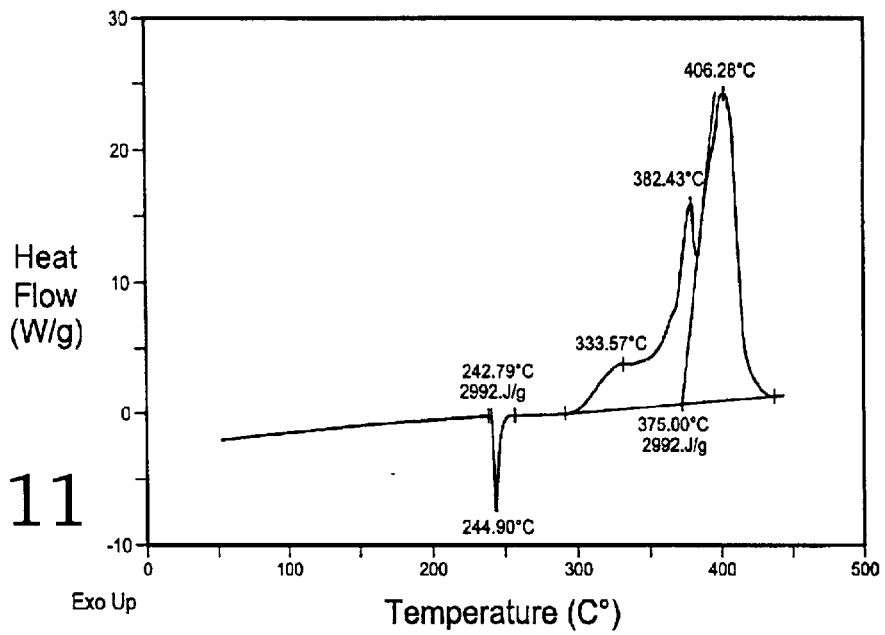
Figure 12:
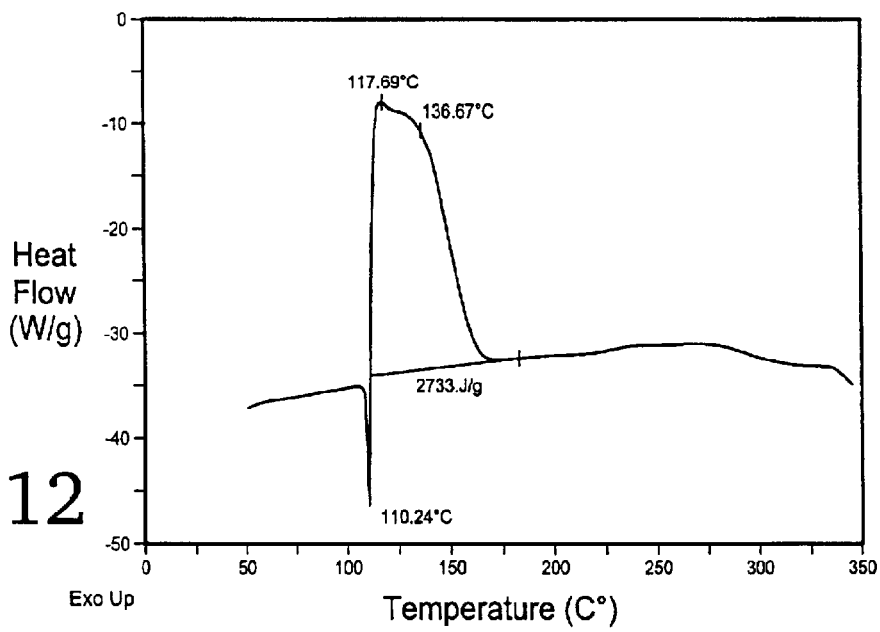
Figure 13:
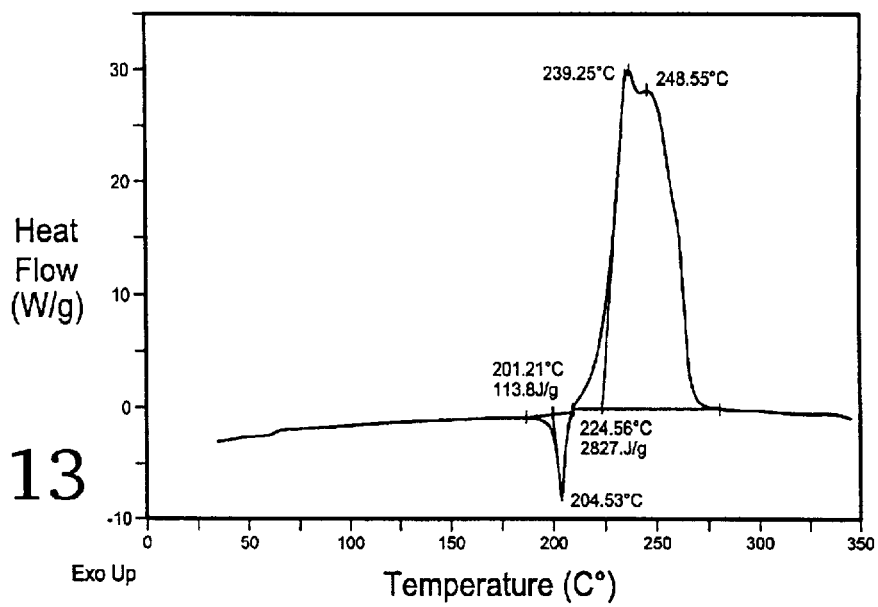
Figure 14:
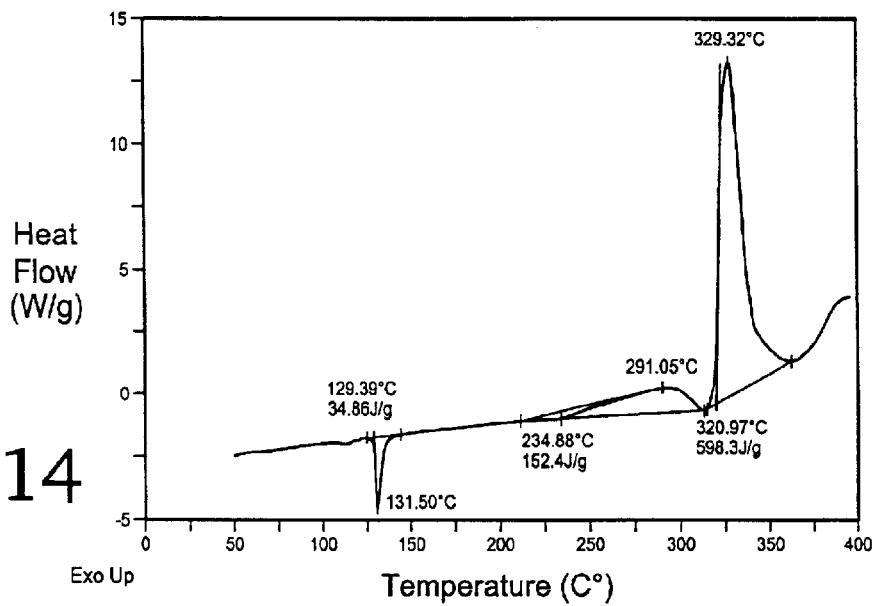
Figure 15:
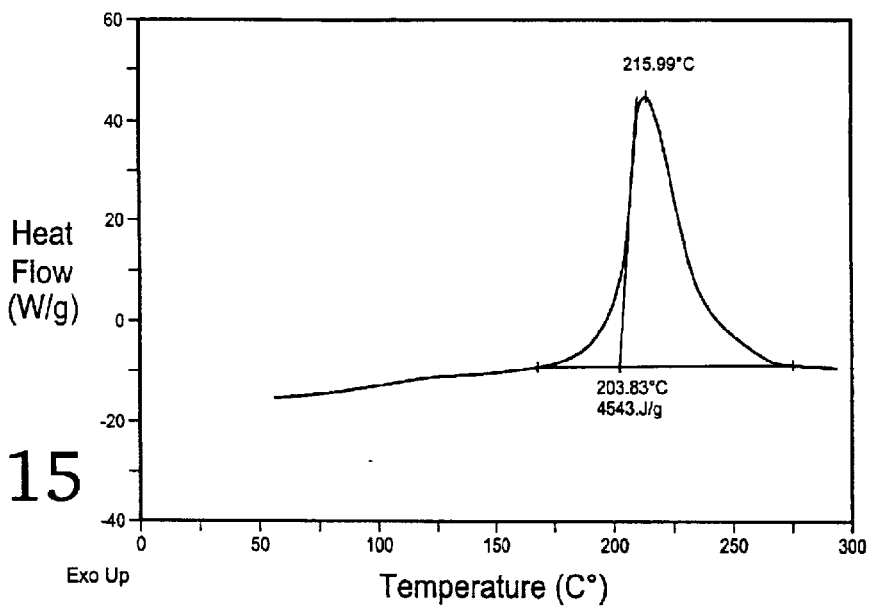
Figure 16:
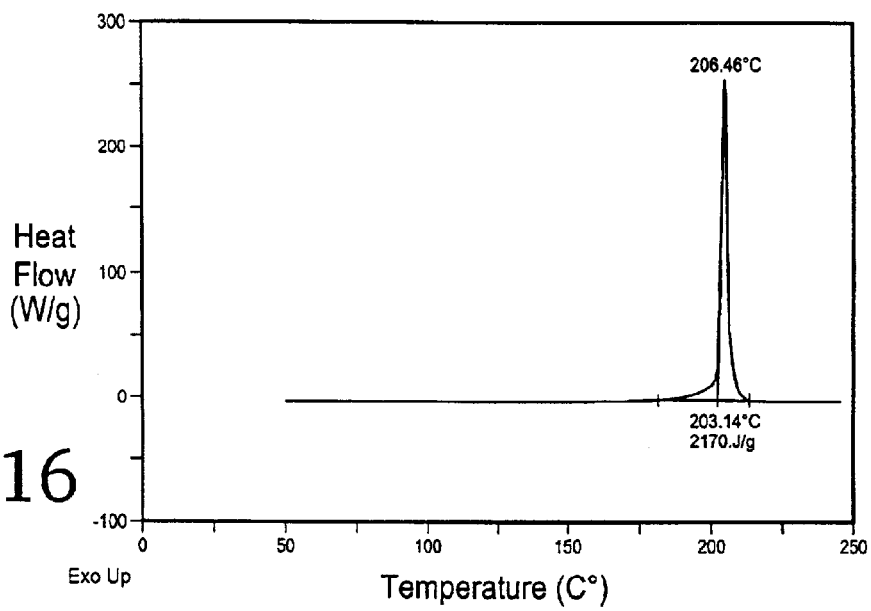

FIGS. 5 to 16 show DSC thermograms for the following explosives: C4 plastic explosive, triacetone triperoxide (TATP), diacetone diperoxide (DADP), hexamethylenediamine triperoxide (HMTD), ammonium nitrate, urea nitrate, ammonium perchlorate, benzoyl peroxide, trimethylenetrinitramin (RDX), Black Powder (BP), Remington Smokeless Powder (RSP), and military specification ammunition powder (MSAP). For a general reference about explosives such as these, see, e.g., J. Kohler and R. Meyer *Explosives* 4th ed. (VCH Publishers, New York, 1993). As shown in the figures, each sample exhibits a pronounced exotherm. In particular, FIG. 5 shows an exotherm at about 250° C. for C4 plastic explosive. FIG. 6 shows an exotherms at about 163° C. and 230° C. for TATP. FIG. 7 shows an exotherm at about 235° C. for DADP. FIG. 8 shows an exotherm at about 162° C. for HMTD. FIG. 9 shows an exotherm at about 172° C. for ammonium nitrate. FIG. 10 shows two exotherms at about 148° C. and 232° C. for urea nitrate. FIG. 11 shows an exotherm at about 390° C. for ammonium perchlorate. FIG. 12 shows an exotherm at about 125° C. for benzoyl peroxide. FIG. 13 shows an exotherm at about 245° C. for RDX. FIG. 14 shows an exotherm at about 330° C. for Black Powder. FIG. 15 shows an exotherm at about 216° C. for Remington Smokeless Powder. FIG. 16 shows an exotherm at about 207° C. for the Military Ammunition Powder.

Figure 17:
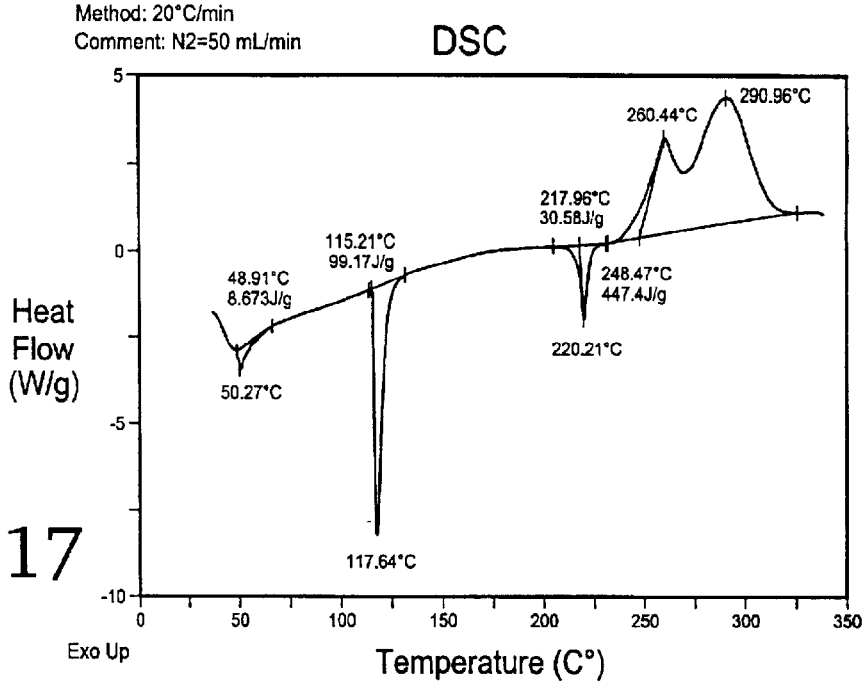

Other energetic materials include semi-volatile detection agents which are mixed with commercial explosives as a means of identifying the nature and source of the explosive. One such detection agent is 2,3-Dimethyl-2,3-dinitrobutane (DMDNB), which is an energetic material, but not an explosive. FIG. 17 shows a DSC thermogram for DMDNB, which shows an exotherm at about 290° C. For a reference on such detection agents, see, e.g., D. E. G. Jones et al., *Journal of Thermal Analysis,* 44:533–546, 1995.

Based on the results, testing samples at temperatures ranging from about 100° C. up to about 400° C. will provide positive results without interference from exotherms due to combustion or oxidation of non-energetic materials in the presence of oxygen.

DSC Patterns of Mixed Samples

Figure 18:
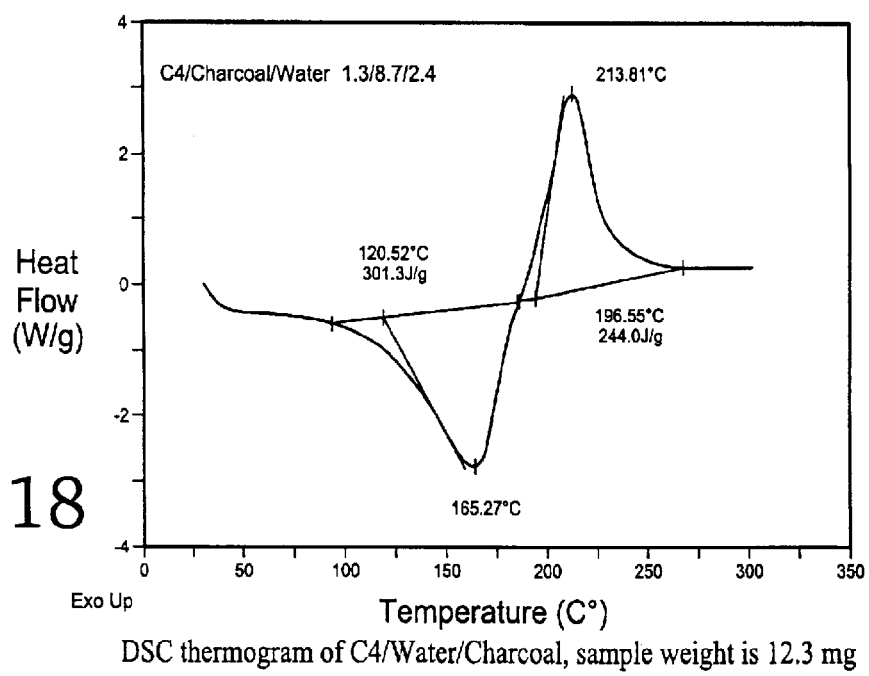
Figure 19:
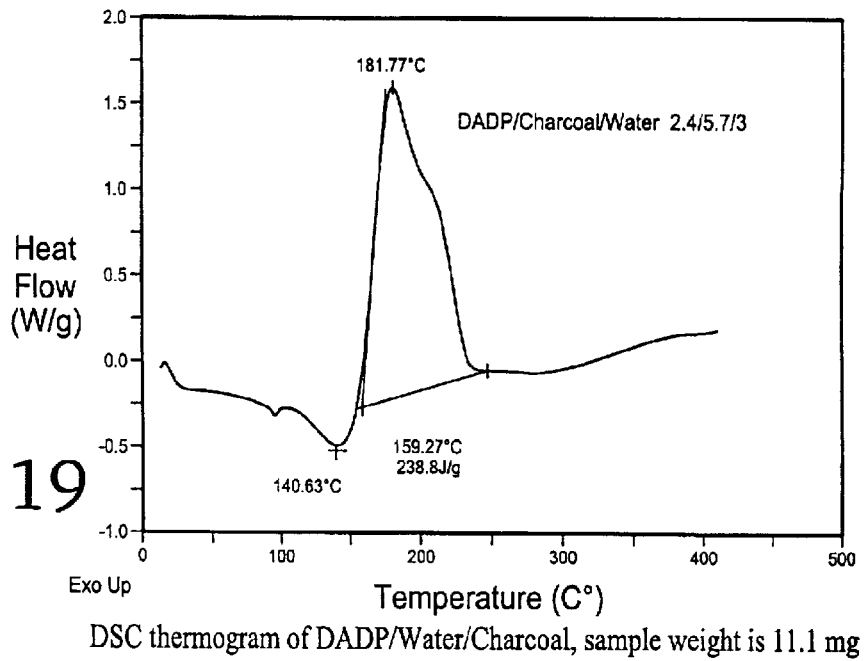
Figure 20:
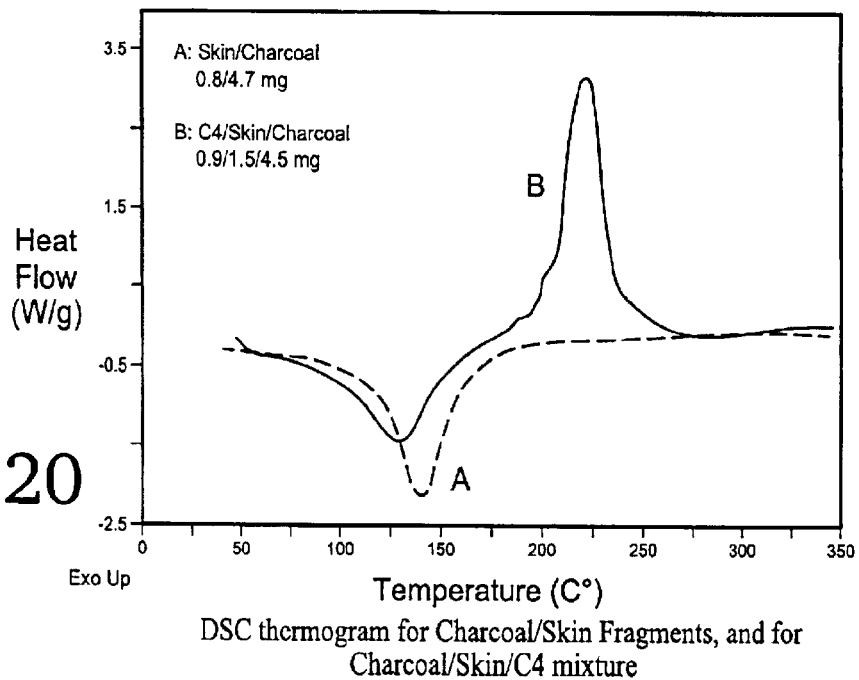

Explosive agents are typically mixed with other materials and, in general, samples will also include contaminants from the ambient environment, such as water, gases, and innocuous vapors and air-borne particles. FIGS. 18 and 19 show DSC thermograms for C4 plastic explosive and HMTD, respectively, mixed with charcoal and premoistened with water. Although both thermograms exhibit endotherms due to the evaporation of water, in each case there remains a distinct exotherm, which indicates the presence of the explosive. FIG. 20 shows a pair of DSC scans of human skin particles mixed with charcoal without explosive (thermogram A) and with C4 plastic explosive (thermogram B). Again, the presence of an energetic material in the sample produces an exotherm, which indicates the presence of the energetic material.

Detection Limits

Figure 21:
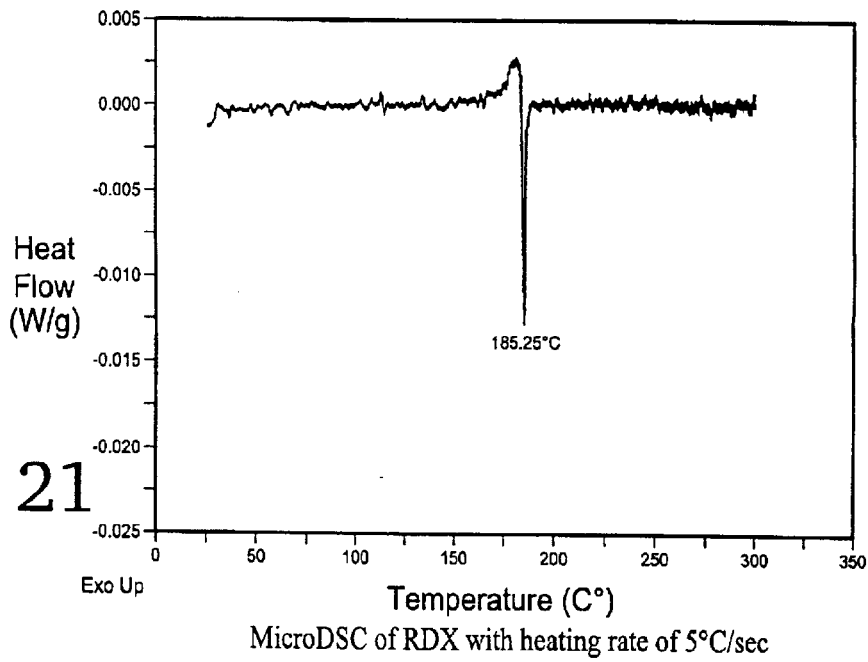
Figure 22:
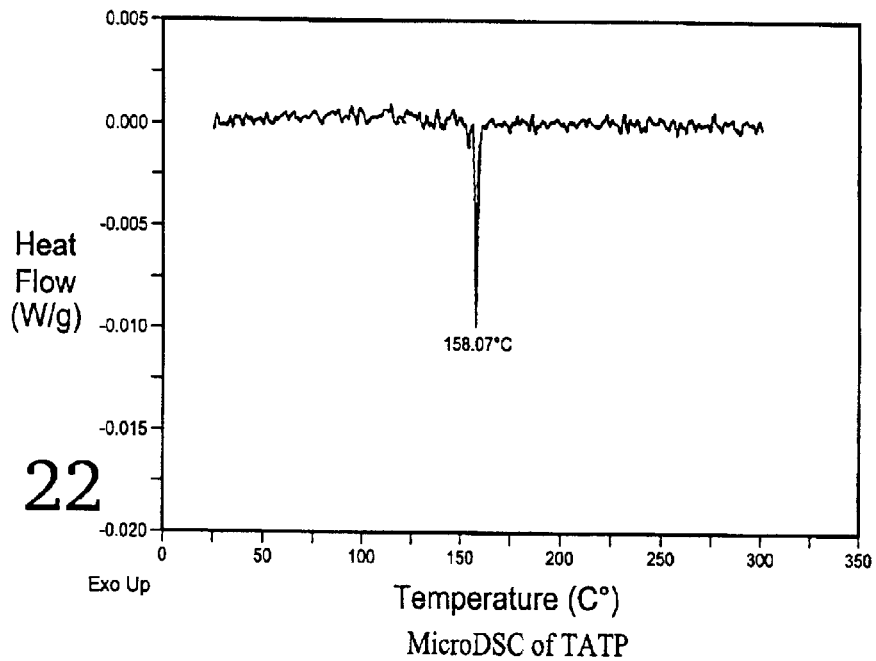
Figure 23:
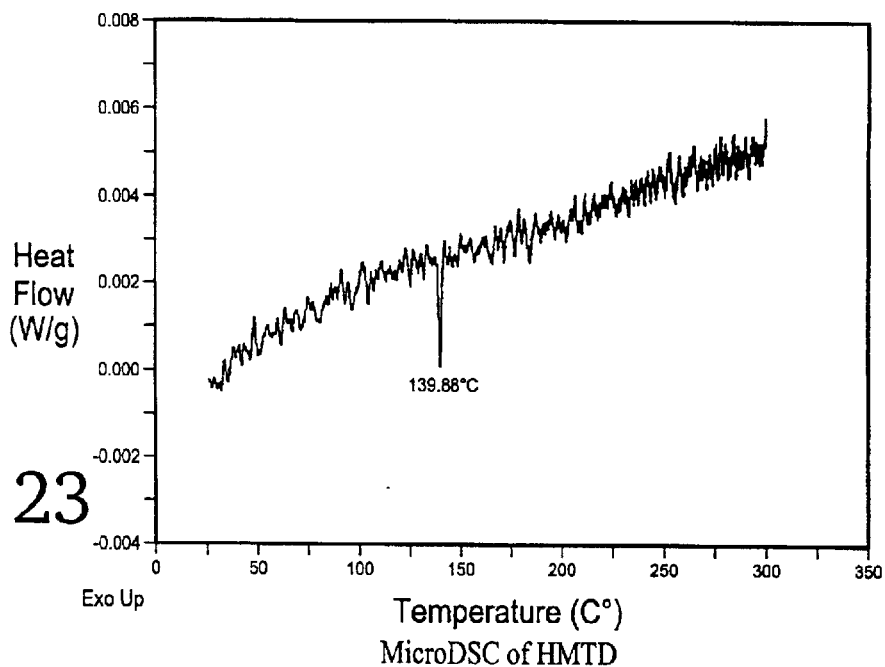

The previous DSC scans were based on modest quantities of explosive materials, e.g., hundreds of micrograms. Using more advanced DSC technology, such as the commercially available microDSCs from TA Instruments, described previously, much smaller quantities can be detected. To demonstrate, DSC scans were prepared using the Model 2990 microDSC from TA Instruments. Samples of explosives having masses estimated to be between 10 to 100 picograms were introduced into the microDSC. FIGS. 21 to 23 show the measured DSC thermogram for RDX, TATP, and HMTD, respectively, using the microDSC instrument. Note that for this particular instrument exotherms appear as negative peaks. Even with the small quantity of explosive in each sample, the DSC thermogram clearly shows an exotherm indicating the presence of an energetic material in the sample. In view of the data, it is reasonable that samples containing as little as 1 picogram of explosive could be detected. Furthermore, using collection systems such as those described further below, which can concentrate up to a million parts of air into 1 part of water, even trace amounts of explosives obtained from air vacuumed from luggage or directly from passengers as they walk through a detector can be detected.

Effects of Heating Rates

Figure 24:
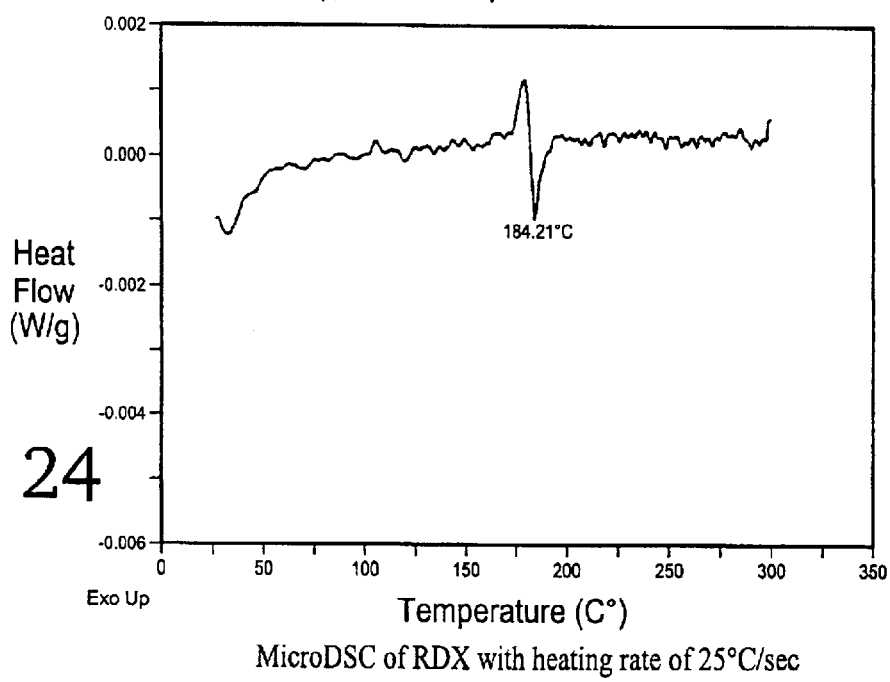

In general, the heating rate during the thermal analysis affects the specific features of the measured thermogram. For example, FIG. 24 is a microDSC scan of RDX at a fast heating rate of 25° C./sec, relative to the previous microDSC scan of RDX shown in FIG. 21, which had a heating rate of 5° C./sec. As shown in FIG. 24, the faster heating rate produces a less pronounced exotherm and lowers the temperature at which the exotherm occurs by about 1° C. Nonetheless, the exotherm is clearly apparent, indicating that very fast scans can be used. As a result, rapid exothermal detection of explosives is possible.

Collection Systems

The collection system 210 in the explosives detector of FIG. 2 can take many forms. For example, an airstream can be driven through a filter, such as a charcoal filter, to collect airborne particles in the airstream. Alternatively, a gauze tissue can be used to wipe the surfaces of articles that potentially contact explosive agents. Particles trapped by the filter or tissue can be extracted therefrom and condensed by using an air stream, an extraction fluid, electrostatic techniques, or some combination thereof. In general, suitable collection systems are known in the art and many are used in conjunction with alternative explosives detectors. See, for example, the collection systems in U.S. Pat. Nos. 5,092,218 and 5,345,809, which describe suitable collection systems.

Another suitable collection system is a space charged atomizing electrostatic precipitation (SCAEP) air sampler such as the SCAEP Air Sampler/Concentrator commercially available from Team Technologies (Newton, Mass.). The instrument concentrates minute quantities of airborne particles in large quantities of air into relatively small quantities of water, e.g., up to a million parts of air into 1 part of water, by combining conventional air scrubbing with electrostatic precipitation. Contaminated air particles are sampled countercurrent to a charged liquid aerosol spray that intercepts particles, vapors, and gases, and delivers them to the collection fluid.

Figure 25:
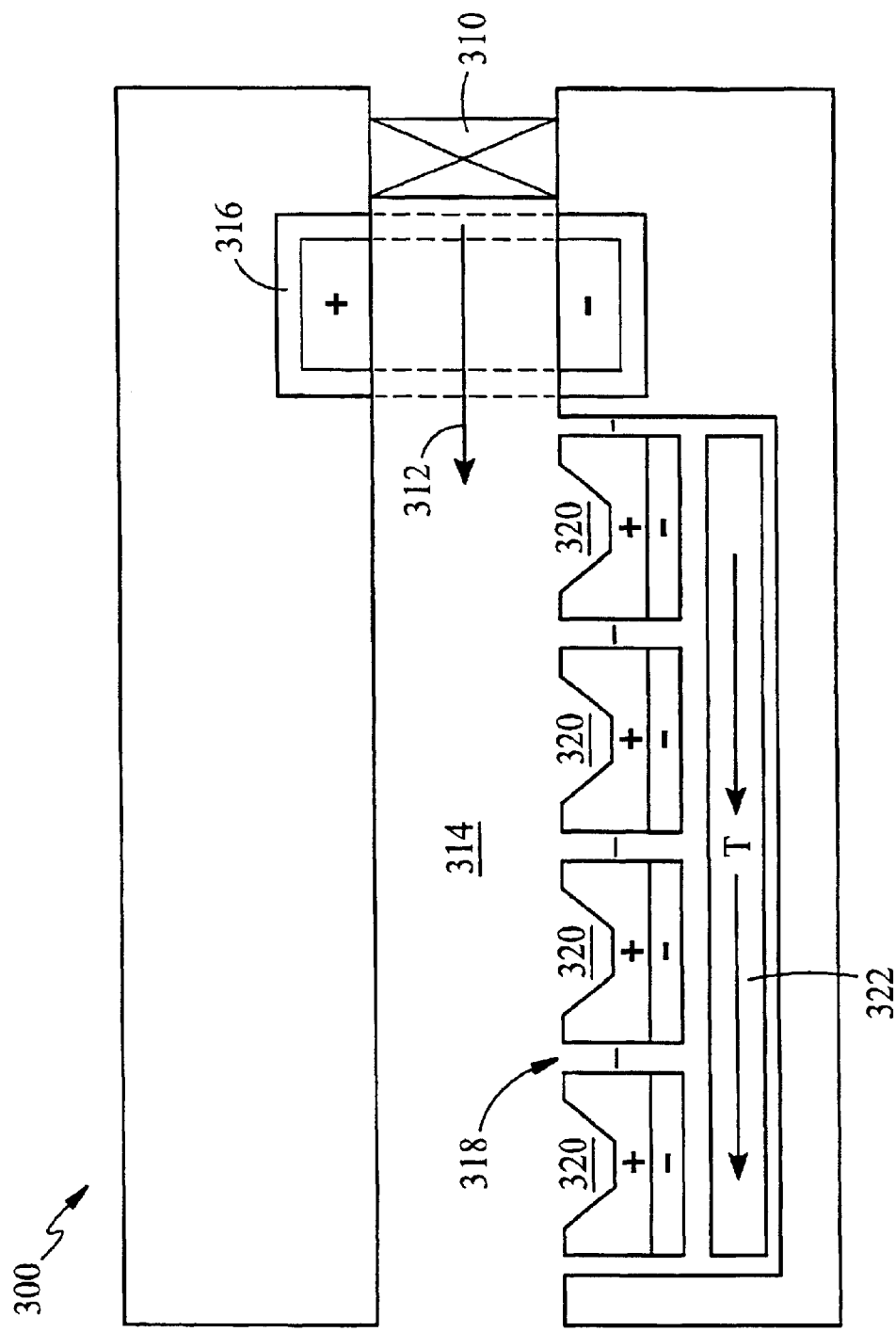
FIG. 25 is a schematic of a collection system for the explosives detector of FIG. 2.

Another suitable collection system 300 is shown in FIG. 25. A pump 310 draws an air stream 312 into a collection chamber 314. Air stream 312 first passes though the electrodes of an electrostatic voltage source 316, which electrostatically charges the particles in the air stream. Thereafter, air stream 312 passes above a conveyor belt 318 having a series of conical collection cups 320, which have an electrostatic charge opposite to that of the particles. Attractive forces between the opposite charges force the particles to precipitate into cups 320, which concentrate them. Thereafter, conveyor belt 318 delivers the concentrated sample to a thermal analysis instrument, such as a differential scanning calorimeter.

Alternatively, organic solvent extraction can be used in place of electrostatic precipitation to concentrate the sample. In such a case, collection cups 320 carry a volatile organic solvent, such as methylene chloride, perflouroalkanes, hydrofluorochloroalkanes, substituted ethers, or esters. The organic solvent collects and dissolves the airborne vapors and particles. As conveyor belt 318 moves, it passes over heating elements 322 that evaporate the volatile collection fluid, thereby concentrating the collected particles.

Other collection systems can also be used with the new explosives detectors and methods. For example, particles suspended in water, such as those electrostatically precipitated on a running water film or aerosol, can be removed from the water and concentrated by extraction using a volatile organic solvent, such as methylene chloride, perflouroalkanes, hydrofluorochloroalkanes, substituted ethers, or esters. Also, depending on the end-use application, the collection system can be implemented in various ways, such as a hand-held device or wand, which would be useful to scan luggage or passengers, a continuous air sampling system, which would be useful in an airport or airplane cargo bay, or as a laboratory device for forensic testing.

Identification of Explosives and Drugs

As described above, thermal analysis of an unknown sample can be used to detect the presence of explosive or energetic agents in a test sample of unknown composition. Thus, if oxygen is excluded from the sample while it is undergoing DSC heating or if oxygen is present but temperatures are kept less than those necessary for combustion, an exothermic peak is a positive and reliable indication that an energetic material is present in the sample. Conversely, a thermogram having only endothermic peaks is a reliable indication that an energetic material is not present in the sample.

When the detection system of FIG. 2 detects an energetic agent or explosive in a sample, it may also be useful to determine which particular energetic material has been detected, i.e., to identify the energetic material. As seen in the thermograms of FIGS. 3 to 24, different materials have characteristic thermograms. In particular, the thermograms of each explosive and energetic material have one or more exotherms at temperatures that are characteristic for that particular material. Thus, not only can explosives be generally detected, particular explosives can be identified. In addition, other features of the thermogram, such as its endotherms, can be used to further distinguish one energetic material from another.

For example, based on the thermal analyses described above, the following characteristics can be assigned to common explosives C4, DADP, TATP, HMTD, and RDX. C4 has an exotherm at about 210–220° C. and an endotherm at about 120–130° C. DADP has an exotherm at about 175–185° C. and an endotherm at about 130–140° C. TATP has an exotherm at about 195–205° C. and an endotherm at 135–145° C. HMTD has an exotherm at 135–145° C. and RDX has an exotherm at 180–190° C. Such information can be stored in a reference library 228 in analyzer 220 of the detection system in FIG. 2.

During operation, the analyzer would first determine whether the measured thermogram for a particular sample contained an exotherm. If so, the analyzer would recognize the presence of an explosive or energetic material in the sample. Thereafter, the analyzer would determine the temperature ranges of the exotherms and endotherms in the thermogram and compare those temperatures with temperatures in the reference library. If the measured temperatures agree with those for a particular material in the reference library, the analyzer would identify that energetic or explosive material as the one present in the test sample. In addition, the analyzer can compare other features of the exotherms and endotherms such as their shape, or the amount of heat released ($\Delta H_{exo}$) or absorbed ($\Delta H_{endo}$), respectively. Alternatively, the analyzer can compare the entire thermogram of the test sample with reference thermograms stored in the analyzer, and determine the best match. As described previously, the analyzer can be, e.g., a computer storing software that causes a processor in the computer to carry out the steps described above or a dedicated electronic circuit programmed to operate similarly. Reference library 228 can be stored in any type of standard data storage, e.g., on a hard disk of a computer or a CD ROM.

As described previously, the precise features of the thermogram can vary with the thermal analysis protocol, e.g., heat rates and sample size. Thus, the thermogram for the test sample should be measured using the same protocol as that used to obtain the reference thermograms. In addition, the precise features of the thermogram can depend on what combination of materials is present in the sample. Thus, the reference library can also include reference thermograms of explosives or other controlled substances mixed with other materials, in varying amounts. For example, the reference library can include reference thermograms for mixtures of explosives such as C4, Black Powder, and ANFO, with other materials.

In practice, the circumstances for identification would differ from those of detection. The detection method and system described above provides rapid detection of the presence of an energetic material in an unknown sample, as may be necessary, e.g., for airport security. The identification method and system, however, would typically be used under circumstances where forensic identification of the composition of a sample is required. In such cases, possible compositions for the sample may already be known and, relative to the time available for, e.g., an airport security check (to detect explosives), there may a significant amount of time available for the forensic identification. Thus, a suitable set of reference thermograms can be selected and compared with a high resolution DSC scan of the test sample. If necessary, additional reference thermograms can be measured to confirm a positive identification.

The thermal analysis techniques described above can also be used to identify drugs, e.g., cocaine, heroin, marijuana, and hashish, and other controlled substances. In such cases and unlike energetic materials, the drugs do not exhibit an anaerobic exotherm that permits them to be generally distinguished from non-drugs. However, the thermogram features of each particular drug enable the detection and identification of that drug in a sample of unknown composition in the same way as was described in the previous section with regard to identifying particular explosives.

Figure 26:
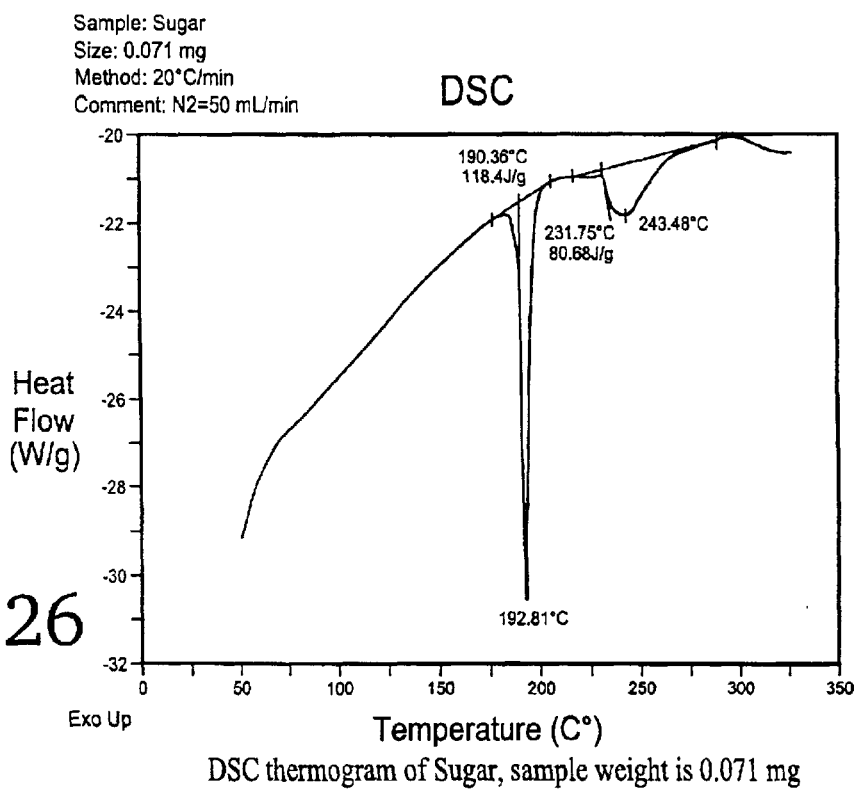
FIGS. 26 to 30 are differential scanning calorimetery thermograms relating to the identification of various drugs.
Figure 27:
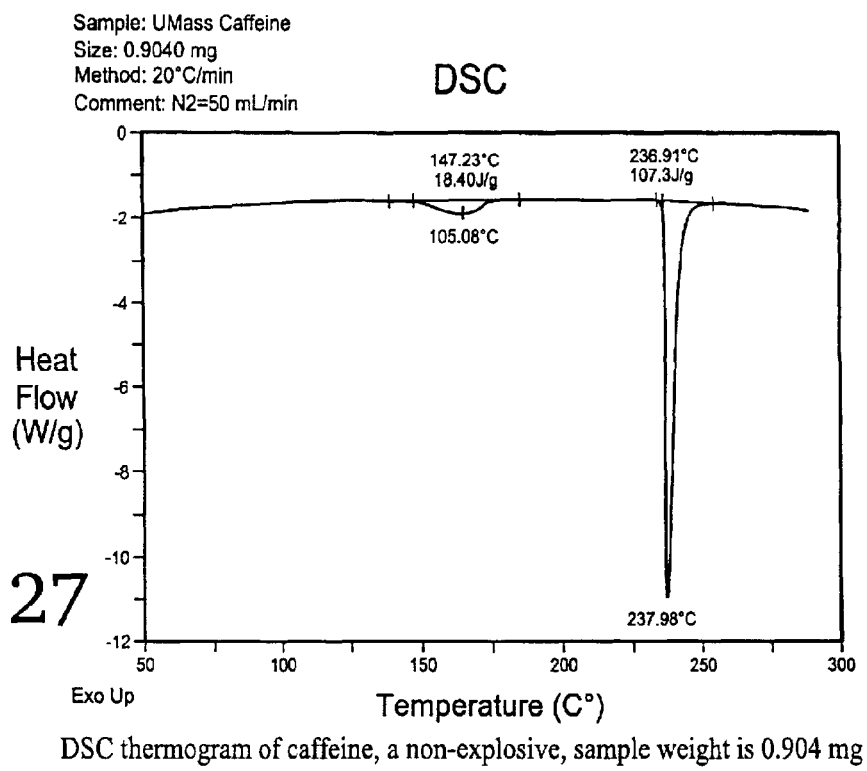

For example, FIGS. 26 and 27 show DSC thermograms for sugar and caffeine, respectively. As expected, neither exhibits an exotherm, however, the temperatures of their endotherms distinguish one from the other, and more generally, their thermogram patterns also distinguish one from the other. In particular, the drug caffeine exhibits a strong endotherm at about 238° C. and a weaker endotherm at about 165° C., whereas sugar exhibits a strong endotherm at about 193° C. and a weaker endotherm at about 244° C.

Figure 28:
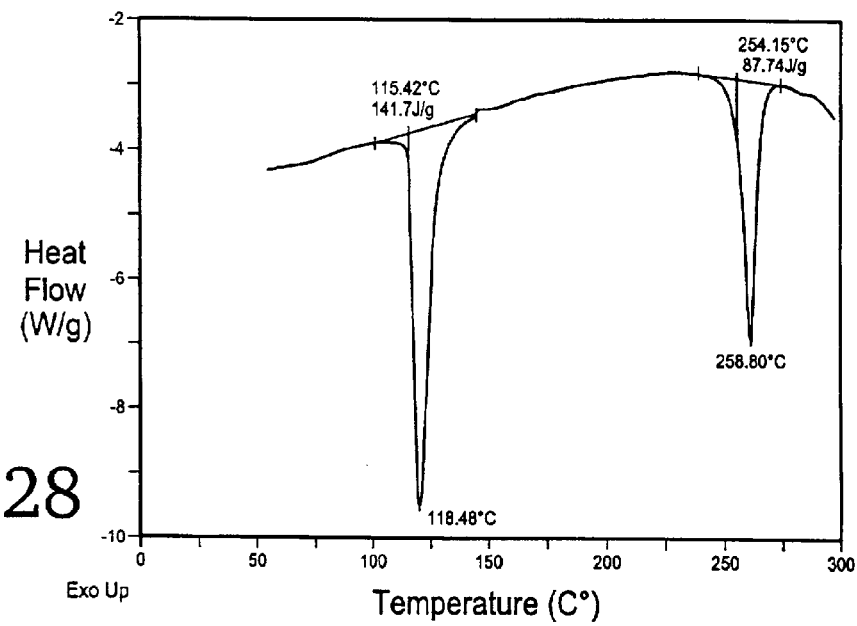
Figure 29:
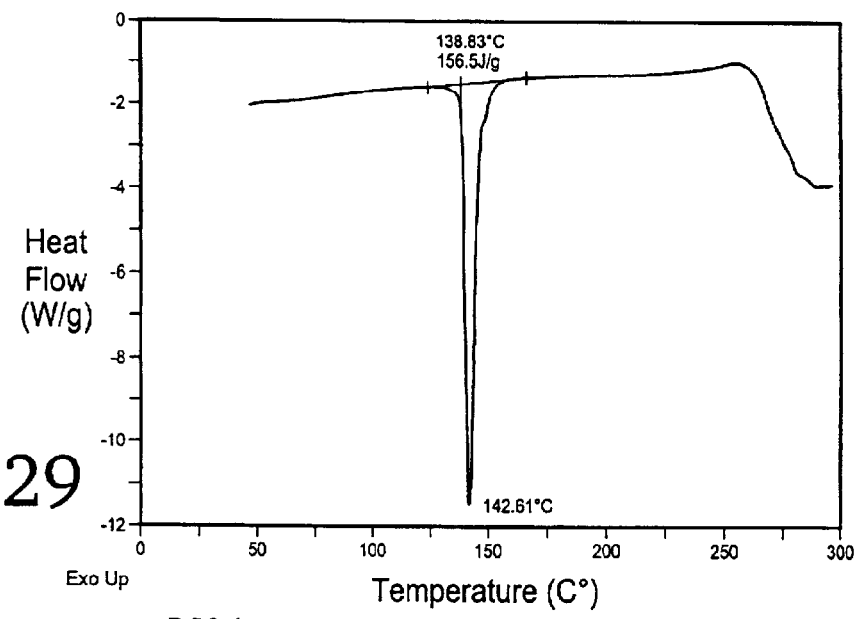
Figure 30:
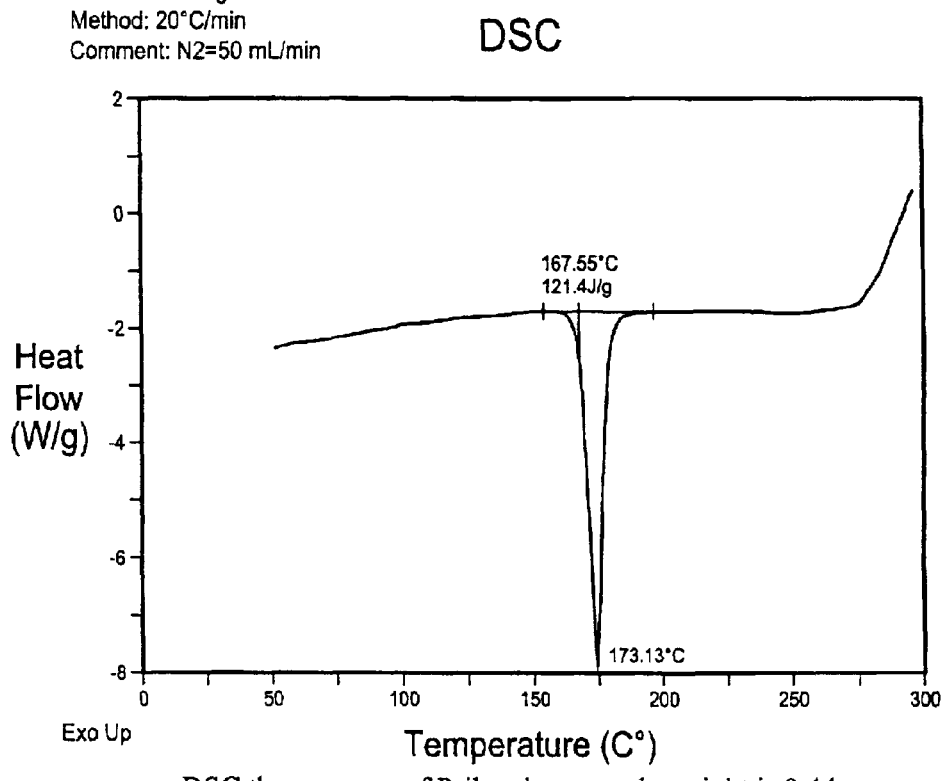

Such features can be stored in a reference library and compared with the features measured for a test sample of unknown composition to identify which, if any, of the reference materials are present in the test sample. FIGS. 28 to 30 show measured thermograms for the drugs bupiavacaine, tetracaine, and prilocaine (which is used as an anesthetic), respectively. Once again the temperatures of their respective endotherms distinguish them from other material.

of the reference samples was selected. During the scan, the operator of the DSC observed an endotherm around 166° C., suggesting that the selected sample was either urea nitrate or caffeine. Thereafter an exotherm was observed at 175° C., and the DSC operator unambiguously confirmed that the selected sample was the explosive urea nitrate.

Other Embodiments

It is to be understood that while the invention has been described in conjunction with the detailed description

TABLE 1

Summary of DSC Data

| Compound | Endotherm Temperatures (° C.) | $\Delta H_{endo}$ (J/g) | Exotherm Temperatures (° C.) | $\Delta H_{exo}$ (J/g) |
|---|---|---|---|---|
| TATP | 97–99 | 79–85 | 162–164/196–220/230–240 | 2887 |
| DADP | 133 | 189 | 238- | 2500 |
| HMTD | — | — | 163–164 | 3000 (est.) |
| RDX | 205 | 110 | 239–241/248–250 | 2830 (total) |
| FFF9 | 132 | 35 | 291/329 | 152/598 |
| Mil. Spec. Ammo. | — | — | 206 | 2170 |
| Remington Smokeless | — | — | 216 | 4543 |
| Urea Nitrate | 166 | 107 | 174 | 555 |
| C-4 | —/204 | 126 | 249/— | 2489 (total) |
| Benzoyl Peroxide | 110 | — | 118, 137 | 2740 (total) |
| Ammonium Perchlorate | 245 | 82 | 334/382/406 | 3000 (total) |
| 2,3-Dimethyl-2,3-dinitrobutane | 50/118/220 | —/100/31 | 260/291 | 447 (total) |
| Caffeine | 238 | 107 | — | — |
| Bupivacaine | 119/260 | 142/88 | — | — |
| Tetracaine | 143 | 156 | — | — |
| Prilocaine | 173 | 168 | — | — |
| Benzoic Acid | 125/232 | 117/108 | — | — |
| Sugar | 193/243 | 118/231 | — | — |

Table 1 tabulates the thermogram features of specific materials that were measured using the DSC and microDSC techniques described above. The features listed below are for single-component samples containing only the listed compound under the conditions specified above for each sample. Such data can be used (and added to) in a reference library stored in the analyzer to identify or confirm the composition (e.g., explosive, drug, or contraband material) of a test sample. Additional data stored in the reference library can include thermogram features of multi-components samples containing mixtures of explosives, drugs, or contraband materials with other materials. In the table below, values for $\Delta H_{exo}$ and $\Delta H_{endo}$ with "total" in parenthesis are values that integrate over multiple overlapping exotherms and endotherms, respectively. Otherwise the values for $\Delta H_{exo}$ and $\Delta H_{endo}$ refer to specific exotherms and endotherms, respectively.

To test the ability of thermal analysis measurements to identify an otherwise unknown sample, the following test was performed. A sample was secretly selected from one of the following reference samples urea nitrate, RDX, sugar, and caffeine. Reference DSC scans for these reference samples were recorded earlier and are shown in FIGS. 10, 21, 26, and 27, respectively. The selected sample had a mass of about 0.26 mg. A conventional DSC was used under nitrogen with a heating rate of 20° C./minute to heat the selected sample from room temperature to about 350° C. and record the DSC scan. The operator of the DSC did not which thereof, that the foregoing description is intended to illustrate and not limit the scope of the invention, which is defined by the scope of the appended claims.

For example, additional analytical techniques can aid the identification of the specific energetic material or drug. For example, the microDSC from TA Instruments described previously also includes an atomic force microscopy (AFM) head with a thermal probe that permits measurement of sample topography, thermal conductivity, and thermal diffusivity. Thus, such properties can be measured for a test sample (in addition to the thermogram) and compared with the corresponding properties of reference samples measured by the same instrument. The microDSC also includes a CCD camera that can record images of the test sample to indicate its morphology, which once again can be compared to the morphologies of reference samples to aid identification of the test sample.

Other aspects, advantages, and modifications are within the scope of the following claims.

What is claimed is:

1. A system for detecting the presence of an energetic material in a sample in which the presence of the energetic material is unknown, the system comprising:
    a thermal measuring apparatus which during operation heats the sample and measures heat flow between the sample and its surrounding environment;
    a computer coupled to the thermal measuring apparatus and operative to control the thermal measuring apparatus to:

heat the sample;

measure the heat flow between the sample and its surrounding environment; and produce a thermogram;

said computer further comprising an analyzer comprising software, wherein the software causes the analyzer to analyze the heat flow measured by the thermal measuring apparatus and to determine the presence or absence of a strong exothermal peak in the thermogram, wherein the presence of a strong exothermal peak indicates the presence of the energetic material in the sample and the absence of a strong exothermal peak indicates the absence of any energetic material in the sample.

2. The system of claim 1, wherein the thermal measuring apparatus is a differential scanning calorimeter.

3. The system of claim 1, further comprising a collection apparatus that collects and concentrates the sample.

4. The system of claim 3, wherein the collection apparatus collects and concentrates the sample by electrostatic precipitation.

5. The system of claim 3, wherein the collection apparatus collects and concentrates the sample by solvent extraction.

6. The system of claim 1, wherein the thermal measuring apparatus heats the sample in a substantially anaerobic environment.

7. The system of claim 1, wherein the thermal measuring apparatus heats the sample to a temperature no greater than about 500° C.

8. The system of claim 1, wherein the thermal measuring apparatus heats the sample to a temperature no greater than about 350° C.

9. The system of claim 1, further comprising an alarm or display activated by the analyzer when a strong exothermal peak is identified to signal the presence of an energetic material.

* * * * *